US010682476B2

(12) United States Patent
Curtis et al.

(10) Patent No.: US 10,682,476 B2
(45) Date of Patent: *Jun. 16, 2020

(54) POWDER INHALER, SYSTEM AND METHODS

(71) Applicant: Respira Therapeutics, Inc., Albuquerque, NM (US)

(72) Inventors: Robert M. Curtis, Santa Fe, NM (US); Dan Deaton, Apex, NC (US); James Hannon, Albuquerque, NM (US); Hugh Smyth, West Lake Hills, TX (US); Zhen Xu, Albuquerque, NM (US); Martin J. Donovan, El Paso, TX (US)

(73) Assignee: Respira Therapeutics, Inc., Albuquerque, NM (US)

( * ) Notice: Subject to any disclaimer, the term of this patent is extended or adjusted under 35 U.S.C. 154(b) by 1098 days.

This patent is subject to a terminal disclaimer.

(21) Appl. No.: 14/627,807

(22) Filed: Feb. 20, 2015

(65) Prior Publication Data

US 2015/0314086 A1 Nov. 5, 2015

Related U.S. Application Data

(63) Continuation-in-part of application No. 13/773,325, filed on Feb. 21, 2013.

(Continued)

(51) Int. Cl.
*A61M 15/00* (2006.01)

(52) U.S. Cl.
CPC ...... *A61M 15/0005* (2014.02); *A61M 15/001* (2014.02); *A61M 15/009* (2013.01);
(Continued)

(58) Field of Classification Search
CPC ............ A61M 15/0005; A61M 15/001; A61M 15/0085; A61M 15/0086
See application file for complete search history.

(56) References Cited

U.S. PATENT DOCUMENTS 2,534,636 A 12/1950 Stirn
2,579,280 A * 12/1951 Trumbour ............. A61M 15/00
128/203.15

(Continued)

FOREIGN PATENT DOCUMENTS

CN 1859938 A 11/2006
CN 101856531 A 10/2010
(Continued)

OTHER PUBLICATIONS

International Search Report and Written Opinion for International Patent Application No. PCT/US2016/013456 dated Mar. 17, 2016, 19 pages.

(Continued)

*Primary Examiner* — Joseph D. Boecker
(74) *Attorney, Agent, or Firm* — Kilpatrick Townsend & Stockton LLP

(57) ABSTRACT

A dry powder inhaler includes a powder storage element configured to hold a powdered medicament and an inlet channel receives powdered medicament from the powder storage element that is entrained in an airflow. The inlet channel has a first diameter and defines an opening. The inhaler includes a dispersion chamber that receives the airflow and the powdered medicament from the opening. The dispersion chamber has a second diameter. The inhaler includes an actuator housed within the dispersion chamber. The actuator oscillates within the dispersion chamber when exposed to the airflow to deaggregate the powdered medicament entrained by the airflow passing through the dispersion chamber. A ratio between the first diameter and the second diameter is between about 0.40 and 0.60 such that an audible sound is produced as the actuator oscillates. The inhaler includes an outlet channel through which the airflow and powdered medicament exit the inhaler.

4 Claims, 30 Drawing Sheets

Related U.S. Application Data

(60) Provisional application No. 62/103,485, filed on Jan. 14, 2015, provisional application No. 61/942,954, filed on Feb. 21, 2014, provisional application No. 62/089,741, filed on Dec. 9, 2014, provisional application No. 61/601,400, filed on Feb. 21, 2012, provisional application No. 61/664,013, filed on Jun. 25, 2012.

(52) U.S. Cl.
CPC .... *A61M 15/0035* (2014.02); *A61M 15/0045* (2013.01); *A61M 15/0086* (2013.01); *A61M 15/0091* (2013.01); *A61M 2202/064* (2013.01); *A61M 2205/581* (2013.01)

(56) References Cited

U.S. PATENT DOCUMENTS

| | | | |
|---|---|---|---|
| 2,642,063 | A | 6/1953 | Brown |
| 3,837,341 | A * | 9/1974 | Bell ................ A61B 5/087 |
| | | | 128/203.15 |
| 3,888,252 | A * | 6/1975 | Side .............. A61M 15/0028 |
| | | | 128/203.15 |
| 3,888,253 | A | 6/1975 | Watt |
| 4,706,663 | A * | 11/1987 | Makiej ............ A61M 15/00 |
| | | | 128/200.18 |
| 4,841,964 | A | 6/1989 | Hurka et al. |
| 4,889,114 | A * | 12/1989 | Kladders ........ A61M 15/0028 |
| | | | 128/203.15 |
| 4,995,385 | A | 2/1991 | Valentini et al. |
| 5,513,630 | A * | 5/1996 | Century .......... A61M 15/0028 |
| | | | 128/203.12 |
| 6,230,707 | B1 | 5/2001 | Horlim |
| 8,651,104 | B2 | 2/2014 | Donovan et al. |
| 9,492,625 | B2 * | 11/2016 | Smyth ............. A61M 15/0028 |
| 10,463,815 | B2 * | 11/2019 | Curtis ............. A61M 15/0086 |
| 10,525,216 | B2 * | 1/2020 | Curtis ............. A61M 15/003 |
| 2002/0006316 | A1 | 1/2002 | Schuler et al. |
| 2004/0069303 | A1 | 4/2004 | Brown |
| 2004/0089300 | A1 * | 5/2004 | Miyamoto ........ A61M 15/0028 |
| | | | 128/203.15 |
| 2005/0081850 | A1 * | 4/2005 | Watt ............... A61M 15/0086 |
| | | | 128/203.12 |
| 2008/0035143 | A1 * | 2/2008 | Sievers ............ A61K 9/0075 |
| | | | 128/203.12 |
| 2008/0115785 | A1 | 5/2008 | Eason |
| 2009/0084380 | A1 | 4/2009 | Gieschen et al. |
| 2009/0090362 | A1 | 4/2009 | Harmer et al. |
| 2010/0051023 | A1 * | 3/2010 | Kladders ......... A61M 15/0028 |
| | | | 128/200.21 |
| 2011/0094507 | A1 | 4/2011 | Watchel et al. |
| 2012/0145150 | A1 | 6/2012 | Donovan |
| 2012/0291780 | A1 | 11/2012 | Donovan |
| 2013/0042864 | A1 | 2/2013 | Adler et al. |
| 2013/0213397 | A1 * | 8/2013 | Curtis ............. A61M 15/0045 |
| | | | 128/203.15 |
| 2013/0340747 | A1 | 12/2013 | Donovan |
| 2013/0340754 | A1 | 12/2013 | Donovan |
| 2015/0314086 | A1 | 11/2015 | Curtis |
| 2016/0199598 | A1 * | 7/2016 | Curtis ............. A61M 15/0086 |
| | | | 128/203.15 |
| 2018/0369513 | A1 * | 12/2018 | Hannon .......... A61M 15/0028 |

FOREIGN PATENT DOCUMENTS

| | | |
|---|---|---|
| CN | 102176941 A | 9/2011 |
| EP | 0147755 A2 | 7/1985 |
| JP | 2001070403 A2 | 3/2001 |
| JP | 2003210581 A2 | 7/2003 |
| JP | 2004512103 T2 | 4/2004 |
| JP | 2011212269 A2 | 10/2011 |
| WO | 2005/023348 A2 | 3/2005 |
| WO | 2010/040779 A2 | 4/2010 |
| WO | 2014004250 A1 | 1/2014 |
| WO | 2015/127258 | 8/2015 |

OTHER PUBLICATIONS

Notice of Publication dated Jul. 14, 2016 for U.S. Appl. No. 14/996,011.
International Search Report and Written Opinion for PCT/US2015/016891 dated May 15, 2015, 13 pages.
Partial Supplementary European Search report dated Jul. 9, 2018 in related foreign application No. 16737900.7, 256 pgs.
Extended Search Report dated Oct. 16, 2018 in related foreign application No. 16737900.7, 27 pgs.
Non-Final Office Action dated Oct. 22, 2018 in related U.S. Appl. No. 14/996,011, 29 pgs.
First Office Action for Chinese Application No. 201680015546.1 dated Oct. 9, 2019, all pages.
U.S. Appl. No. 14/996,011, filed Jan. 14, 2016, Non-Final Office Action dated Apr. 29, 2019 in related, all pages.
Office Action, containing references cited by Examiner, dated Dec. 3, 2019 for Japanese Patent Appln No. 2017-537285, all pages.
Office Action for EP 16 737 900.7 dated Mar. 16, 2020, all pages.

* cited by examiner

1kPa

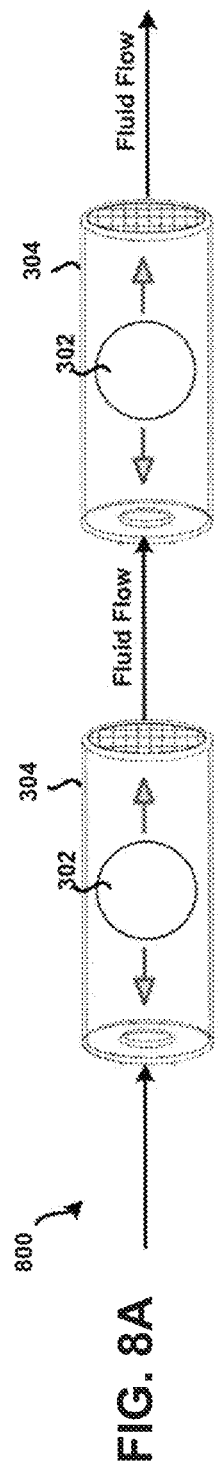
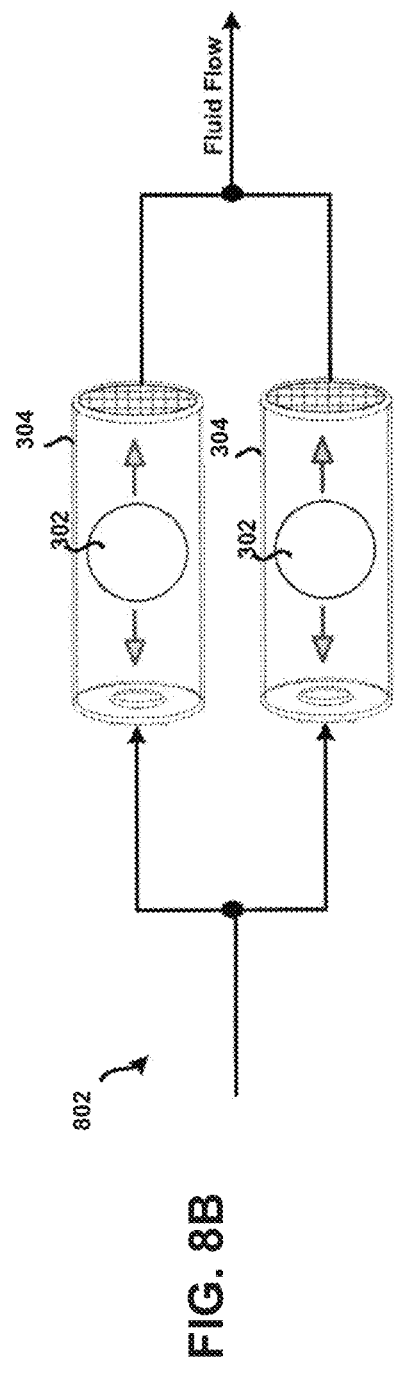
FIG. 8A
FIG. 8B

FIG. 25

POWDER INHALER, SYSTEM AND METHODS

CROSS-REFERENCE TO RELATED APPLICATION

This application is related to and claims priority from U.S. Provisional Patent Application No. 61/942,954, filed on 21 Feb. 2014, entitled "POWDER DISPERSION METHODS AND DEVICES," U.S. Provisional Patent Application No. 62/089,741, filed on 9 Dec. 2014, entitled "PDE5 INHIBITOR POWDER FORMULATIONS AND METHODS RELATING THERETO," and U.S. Provisional Patent Application No. 62/103,485, filed on 14 Jan. 2015, entitled "POWDER DISPERSION METHODS AND DEVICES," this application also claims priority to and is a continuation-in-part of U.S. patent application Ser. No. 13/773,325, filed on Feb. 21, 2013, entitled "INHALER TO DELIVER SUBSTANCES FOR PROPHYLAXIS OR PREVENTION OF DISEASE OR INJURY CAUSED BY THE INHALATION OF BIOLOGICAL OR CHEMICAL AGENTS", which claims benefit to U.S. Provisional Patent Application No. 61/664,013, filed on Jun. 25, 2012, entitled "POWDER DISPERSION DEVICES AND METHODS" and U.S. Provisional Patent Application No. 61/601,400, filed on Feb. 21, 2012, entitled "INHALER TO DELIVER SUBSTANCES FOR PROPHYLAXIS OR PREVENTION OF DISEASE OR INJURY CAUSED BY THE INHALATION OF BIOLOGICAL OR CHEMICAL TERRORISM/WARFARE AGENTS", the entirety of which are hereby incorporated by reference for all purposes.

BACKGROUND

In the field of dry powder inhalers, there is generally a trade-off between performance, as defined by the efficiency of the nominal or loaded dose in the inhaler that is delivered to the lung, and device complexity, in terms of the internal geometry, specifically, the powder flow path that the dose travels as it exits the device. In many instances, inhalers with relatively uncomplicated flow paths may be characterized by poor efficiency, as generally less than 30% of the nominal dose is delivered to the deep lung. Alternatively, inhalers with relatively more complex internal flow paths, may provide increased efficiency, such as less than or equal to 40% of the nominal dose, though the increased complexity of the internal flow path may lead to increased deposition within the inhaler, effectively lowering the overall dose delivered to the patient and contaminating the device. In addition, most dry powder inhalers available today have no means of providing feedback to the user that they have used the device correctly. Incorrect use may cause poor inhaler performance.

SUMMARY

This Summary does not in any way limit the scope of the claimed subject matter.

The present disclosure is directed to a powder dispersion mechanism that is compact, breath-actuated, provides audible feedback, and that is effective or sufficient at promoting efficient particle dispersion across a range of doses such as from, for example, low microgram doses to doses requiring many milligrams. Accordingly, in some embodiments, a powder dispersion mechanism is disclosed that employs an actuator contained within a dispersion chamber. In some embodiments, the powder dispersion mechanism may be breath-actuated while in other embodiments the powder dispersion mechanism may include an external energy source coupled with the patient's inhalation flow stream to induce actuator oscillation. During actuator oscillation the actuator may make an audible sound that could provide feedback for the user of the inhaler.

In one aspect a dry powder inhaler is provided. The inhaler may include a powder storage element configured to hold a powdered medicament and an inlet channel configured to receive powdered medicament from the powder storage element that is entrained in an airflow. The inlet channel may have a first diameter and may define an opening. The inhaler may also include a dispersion chamber that is adapted to receive the airflow and the powdered medicament from the opening of the inlet channel. The dispersion chamber may have a second diameter. The inhaler may further include an actuator housed within the dispersion chamber. The actuator may be configured to oscillate within the dispersion chamber when exposed to the airflow to deaggregate the powdered medicament passing through the dispersion chamber. A ratio between the first diameter and the second diameter may be between about 0.40 and 0.66 such that an audible sound is produced as the actuator oscillates. The inhaler may also include an outlet channel through which the airflow and powdered medicament exit the inhaler for delivery to a patient.

In another aspect, the dry powder inhaler may include a powder storage element configured to hold a powdered medicament and an inlet channel configured to receive powdered medicament from the powder storage element that is entrained in an airflow. The inlet channel may define an opening. The inhaler may include a dispersion chamber that is adapted to receive the airflow and the powdered medicament from the opening of the inlet channel. The dispersion chamber may have a length. The inhaler may further include a bead housed within the dispersion chamber. The bead may be configured to oscillate within the dispersion chamber when exposed to the airflow to deaggregate the powdered medicament passing through the dispersion chamber. The bead may have a diameter such that the length of the dispersion chamber is between about 2 and 3.5 times larger than the diameter of the bead such that an audible sound is produced as the bead oscillates within the dispersion chamber. The inhaler may also include an outlet channel through which the airflow and powdered medicament exit the inhaler for delivery to a patient.

In another aspect, the dry powder inhaler may include a powder storage element configured to hold a powdered medicament and an inlet channel configured to receive powdered medicament from the powder storage element that is entrained in an airflow. The inlet channel may have a first diameter and may define an opening. The inhaler may also include a dispersion chamber that is adapted to receive the airflow and the powdered medicament from the opening of the inlet channel. The dispersion chamber may have a second diameter and a length. The inhaler may further include a bead housed within the dispersion chamber. The bead may be configured to oscillate within the dispersion chamber when exposed to the airflow to deaggregate the powdered medicament passing through the dispersion chamber. The bead may have a third diameter. A ratio between the first diameter and the second diameter may be between about 0.40 and 0.66 and the length may be between about 2 and 3.5 times larger than the third diameter such that an audible sound is produced as the bead oscillates. The inhaler may also include an outlet channel through which the airflow and powdered medicament exit the inhaler for delivery to a patient.

In another aspect, the dry powder inhaler may include a powder storage element configured to hold a powdered medicament and a conically*-shaped or conical frustrum-shaped inlet channel configured to receive powdered medicament from the powder storage element that is entrained in an airflow. The inhaler may also include a dispersion chamber that is adapted to receive the airflow and the powdered medicament from the opening of the inlet channel. The inhaler may further include an actuator housed within the dispersion chamber. The actuator may be configured to oscillate within the dispersion chamber when exposed to the airflow to deaggregate the powdered medicament passing through the dispersion chamber to be entrained by the airflow. The inhaler may also include an outlet channel through which the airflow and powdered medicament exit the inhaler for delivery to a patient.

In another aspect, the dry powder inhaler may include a powder storage element configured to hold a powdered medicament and an inlet channel configured to receive powdered medicament from the powder storage element that is entrained in an airflow. The inhaler may also include a dispersion chamber that is adapted to receive the airflow and the powdered medicament from the opening of the inlet channel. The airflow may be substantially coaxial with a longitudinal axis of the dispersion chamber. The inhaler may further include an actuator housed within the dispersion chamber. The actuator may be configured to oscillate within the dispersion chamber when exposed to the airflow to deaggregate the powdered medicament passing through the dispersion chamber to be entrained by the airflow. The inhaler may also include an outlet channel through which the airflow and powdered medicament exit the inhaler for delivery to a patient. Although not so limited, an appreciation of the various aspects of the present disclosure may be gained from the following discussion in connection with the drawings.

BRIEF DESCRIPTION OF THE DRAWINGS

FIG. 8A shows the device of FIG. 3 with a second chamber in a series configuration according to embodiments.

FIG. 8B shows the device of FIG. 3 with a second chamber in a parallel configuration according to embodiments.

FIG. 25 shows the aerosol performance of a DPI of FIG. 23.

DETAILED DESCRIPTION OF THE DRAWINGS

The present disclosure relates to the field of pulmonary drug or medicament delivery, and more specifically to dry powder inhalers that deliver a powder or medicament into the lungs of a patient. Such a powder dispersion mechanism may include an actuator positioned within a chamber that is arranged and configured to induce a sudden, rapid, or otherwise abrupt expansion of a flow stream upon entering the chamber. During actuator oscillation the actuator may make an audible sound or response that could provide feedback to the user of the inhaler. Characteristics of the audible response may be adjusted based on various geometric properties of an inhaler, as well as material selection. Additionally, at least the chamber may be formed to exhibit one or more features that prevent or at least minimize the accumulation and/or build-up of powder in the chamber with the actuator. This may advantageously prevent the delivery of a macro dose of powder to a patient that may occur when an unintended deposit or residue of powder is broken-up or released during use. An actuator is an element in the inhaler that may oscillate, generally linearly in certain embodiments, along an axis of the dispersion chamber when the patient inhales through the device, such that the actuator does not require an energy source other than a patient's inspiratory maneuver to function. This actuator may take various forms or shapes including a sphere, ball, bead, or bead-like shape. However, the actuator is not limited to these and may take any appropriate shape that results in oscillation.

In some embodiments, a powder dispersion mechanism is disclosed that employs an actuator contained within a dispersion chamber. In some embodiments, the powder dispersion mechanism may include a predominantly straight and/or axial flow path, and may be breath-actuated. This may be referred to as "passive" actuator activation or actuation. During actuator oscillation the actuator may make an audible sound that could provide feedback for the user of the inhaler indicating a successful inhalation effort or successful dose delivery. However, the present disclosure is not so limiting. For example, actuator activation may be "active," where an external energy source is coupled with the patient's inhalation flow stream to induce actuator oscillation. One or more features of the inhaler may be such that a flow profile is generated within the dispersion chamber that prevents or at least minimizes unintended deposition or accumulation of powder within the chamber.

In an aspect, a dry powder inhaler is disclosed. The dry powder inhaler may include a first chamber that is adapted to receive an aerosolized powdered medicament from an inlet channel. A volume of the first chamber may be equal to, greater than or less than the volume of the inlet channel. The dry powder inhaler may include a dispersion chamber that is adapted to receive at least a portion of the aerosolized powdered medicament from the first chamber. The dispersion chamber may hold an actuator that is movable within the dispersion chamber along a longitudinal axis. The dry powder inhaler may include an outlet channel through which air and powdered medicament exit the inhaler to be delivered to a patient. A geometry of the inhaler may be such that a flow profile is generated within the dispersion chamber that causes the actuator to oscillate along the longitudinal axis, enabling the oscillating actuator to effectively disperse powdered medicament received in the dispersion chamber for delivery to the patient through the outlet channel. During actuator oscillation the actuator may generate an audible sound intended for feedback to the user.

Embodiments provide dry powder inhalers configured to produce an audible sound or feedback while delivering acceptable aerosol performance. The audible feedback is sufficiently loud that a user of the inhaler may be alerted when inhalations meet or exceed a minimum amount of flow. Suitable audible sound may be obtained by configuring a ratio ($d_{inlet}/d_{chamber}$) of f an internal diameter of an inlet ($d_{inlet}$) of the inhaler to an internal diameter of a dispersion chamber of the inhaler ($d_{chamber}$) to be within a certain range, by configuring a ratio ($l_{chamber}/d_{bead}$) of a length of the dispersion chamber ($l_{chamber}$) relative to a diameter of the actuator or bead ($d_{bead}$) of the inhaler to be within a certain range, or by certain combinations of both ($d_{inlet}/d_{chamber}$) and ($l_{chamber}/d_{bead}$). These ratios may be specifically selected so that they provide an acceptable audible sound while also ensuring proper aerosol performance (so that the powder can reach the deep lung).

Referring now to FIG. 1, a cross-section of an embodiment of a tubular body 100 having an inlet 102 and a dispersion chamber 104 is shown according to the principles of the present disclosure. In this example, a fluid flow path of the inlet 102 is defined by a first internal diameter 106, and a fluid flow path of the chamber 104 is defined by a second internal diameter 108. Although shown approximately constant in FIG. 1, at least one of the first internal diameter 106 and the second internal diameter 108 may vary in dimension as defined with respect to a longitudinal axis L of the tubular body 100. Further, one or more apertures (not shown) may be formed within the tubular body 100 at particular locations to allow a secondary air supply to enter the tubular body 100 during use to prevent or at least minimize the unintended accumulation or build-up of powder within the tubular body 100. The apertures may be circumferentially aligned, positioned in another pattern, or may be randomly positioned. Additionally, or alternatively, one or more internal surfaces of the tubular body 100 may be formed to exhibit rounded or curved features to prevent or at least minimize the unintended accumulation or build-up of powder within the tubular body 100. For example, some or all of the interior corner surfaces may be curved. In addition to providing desirable fluid flow characteristics, as discussed further below, such configurable internal features or dimensions of the tubular body may be defined so as to provide for a draft angle for injection molding. In some embodiments, an injection molding technique or process may be used to fabricate at least the tubular body 100 of the present disclosure, including like features or elements discussed in further detail below. Other embodiments are possible.

For example, the first internal diameter 106 may taper inwardly, toward and as measured with reference to the longitudinal axis L, beginning approximately at a reference point L1 of the longitudinal axis L and ending approximately at a reference point L2 of the longitudinal axis L. Other embodiments are possible. For example, the first internal diameter 106 may taper inwardly towards the longitudinal axis L beginning approximately at the reference point L2, and ending approximately at the reference point L1. In another embodiment, the second internal diameter 108 may taper inwardly towards the longitudinal axis L beginning approximately at the reference point L3 and ending approximately at the reference point L2. Still other embodiments are possible.

For example, it is contemplated that an internal structural profile of at least one of the inlet 102 and the chamber 104 may be defined, as desired, such as to obtain or otherwise realize particular fluid flow characteristics within the tubular body 100. For example, as depicted in FIG. 1, the tubular body 100 may be arranged and configured such that a sudden flow stream expansion may occur when the relatively "small" cross-sectional fluid flow path of or defined by the inlet 102 opens abruptly into a "larger" cross-sectional fluid flow path of or defined by the chamber 104. In this example, high-energy forces may develop within the chamber 104. In one aspect, this may be due to relatively "low" pressure regions induced by relatively "high" velocity fluid entering the chamber 104, where a portion of the flow stream detaches and recirculation eddies may occur. Other mechanisms may contribute to the development of high-energy fluid flow within the chamber 104 as well. Further, such high-energy fluid flow, along with mechanical impact forces, may disrupt and aerosolize medicament powder agglomerates within the chamber 104 to provide for more effective deposition of medicament into the lungs of a patient. Still other embodiments of the example tubular body 100 are possible as well. For example, in some embodiments, a difference between the reference point L1 of the longitudinal axis L and the reference point L2 may approach zero (0). In this example, the tubular body 100 may consist only of the chamber 104. Here, instead of an "inlet tube," the tubular body 100 may consist of an "inlet hole".

Figure 1:
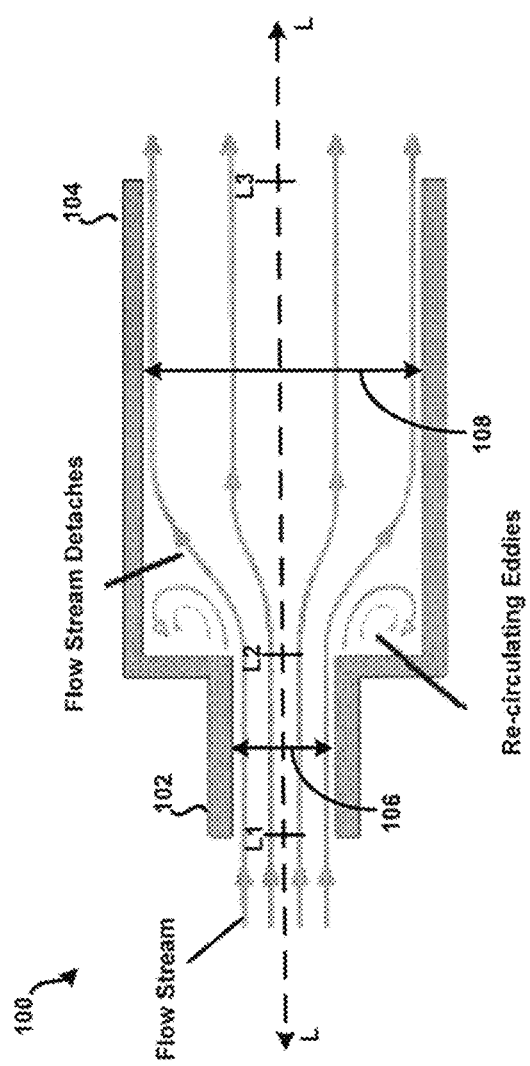
FIG. 1 shows a cross-section of a first example tubular body.

The geometry of the inlet to the dispersion chamber plays a critical role in the resistance of the inhaler. The resistance (R) is a relationship between the pressure drop across the device at a given flow and is defined as $$R = \frac{\sqrt{\Delta P}}{Q}$$

where ΔP is the pressure drop across the device (cm H₂O) and Q is the flow in liters per minute (LPM) at the given ΔP. One embodiment includes a conical inlet, such as inlet 1402 described in FIG. 14. Conical inlets may include inlets that defining two openings of different sizes coupled with one another by one or more tapered walls. For example in FIG. 1, a first distal portion at L1 may taper to a smaller second proximal portion at L2. Experiments have shown that a conical inlet significantly reduces the resistance of the inhaler compared to a tube or inlet hole. An experiment was conducted comparing different inlet geometries with the same inlet diameter 106 and dispersion chamber diameter 108 as defined in FIG. 1: (1) conical inlet and (2) tubular inlet. The inlet diameter 106 was 2.72 mm and the chamber diameter 108 was 5.89 mm and a 4 mm spherical bead was used as the actuator. The length of the chamber from L2 to L3 as shown in FIG. 1 was 10 mm. The conical inlet was shown to have a significantly lower resistance than the tubular inlet as shown in TABLE 1.

TABLE 1

| Geometry | Resistance (cm H₂O)⁰·⁵/LPM |
|---|---|
| Conical | 0.178 |
| Tubular | 0.242 |
| Inlet hole | 0.238 |

Figure 2A:
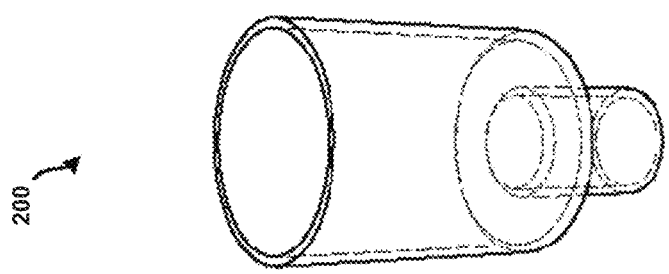
FIG. 2A shows an isometric view of a tubular body.
Figure 2B:
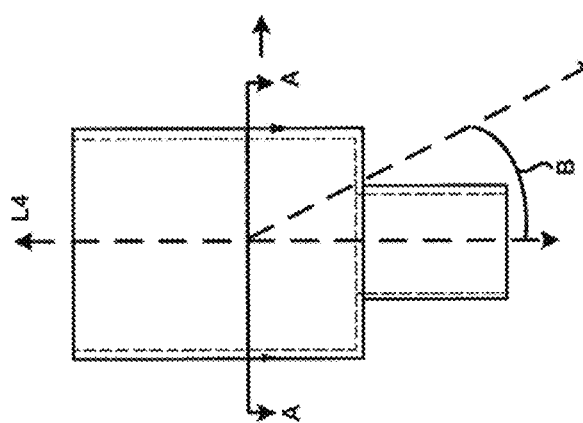
FIG. 2B shows a front view of the tubular body of FIG. 2B.
Figure 2C:
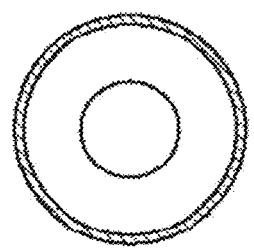
FIG. 2C shows a top view of the tubular body of FIG. 2A.

Referring now additionally to FIGS. 2A-2C, an embodiment of a tubular body 200 is shown in multiple views. In particular, the tubular body 200 is shown in perspective view in FIG. 2A, side view in FIG. 2B, and cross-section view in FIG. 2C. In this example, the cross-section view of FIG. 2C is taken along an axis A-A of the side view of FIG. 2B. Additionally, and as illustrated in FIG. 1, the fluid flow path of or defined by the inlet 102 is coaxially aligned with the fluid flow path of or defined by the chamber 104. This is in contrast with a substantially "off-axis" alignment of the inlet 102 and the chamber 104, illustrated conceptually in FIG. 2B by a finite angle B defined with respect to the longitudinal axis L4. A coaxial alignment may provide a number of advantages over such an "off-axis" alignment, such as facilitating or otherwise assisting in the development of high-energy forces within the chamber 104. The coaxial alignment may further enable the efficient transfer of powder into the chamber 104. However, other embodiments are possible. For example, in some embodiments, a central longitudinal axis of the inlet 102 may be at least slightly offset yet parallel to a central longitudinal axis of the chamber 104. Other benefits and/or advantages associated with the alignment of the inlet 102 and the chamber 104 may be understood from the preceding description provided in connection with FIGS. 1-2C, and from the following description. Although the inlet may be "off-axis" in alignment, the principal component of flow is in the axial direction. Furthermore, swirling or centrifugal flow into the inlet is detrimental to the oscillation of the bead and/or the production of the audible sound response.

Figure 3:
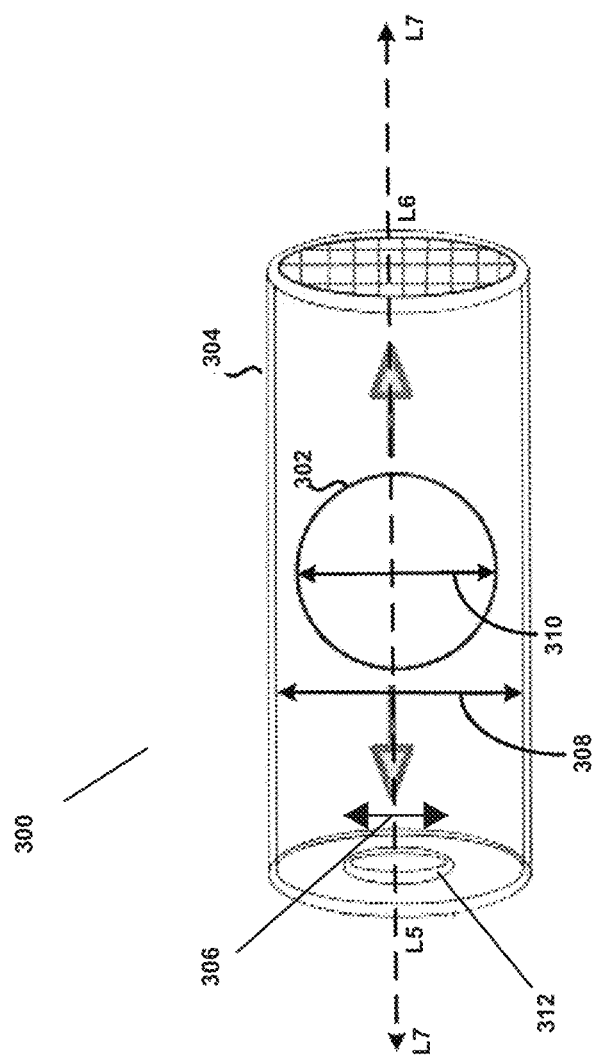
FIG. 3 shows a bead positioned within a chamber of a tubular body.

Referring now to FIG. 3, an actuator or bead 302, which could be shaped as a spherical bead 302 may be positioned within a chamber 304 of a tubular body 300. Tubular body 300 may correspond to the tubular bodies 100 and 200 of FIGS. 1-2. In this embodiment, the bead 302 may be approximately spherical, at least on the macroscale, and oscillate in a manner similar to that described in U.S. application Ser. No. 13/469,963, filed 11 May 2012 and entitled "Bead-Containing Dry Powder Inhaler," the complete disclosure of which is herein incorporated by reference. In some embodiments the actuator may be aspherical, or other shapes which may improve oscillation characteristics of the actuator. Further, a relationship between a diameter 310 of the actuator or bead 302, a first internal diameter 306 of an inlet 312, and a second internal diameter 308 of the chamber 304 may be of the form: $(d_{bead})^2 = (d_{inlet})(d_{chamber})$ where $d_{bead}$ and $d_{inlet}$ and $d_{chamber}$ are of similar order of magnitude. For example, in one embodiment $d_{bead}$ may be about 4.00 mm, $d_{chamber}$ may be about 5.89 mm, and $d_{inlet}$ may be about 2.72 mm within manufacturing tolerance. In this example, a length of the chamber 304, $l_{chamber}$, such as defined by a distance approximately between the reference point L5 and the reference point L6 of the longitudinal axis L7, may be 2 to 3.5 times the diameter 310 of the bead 302.

In some embodiments, the diameter 310 of the bead 302 may be within a range of about 0.5 mm to about 15 mm. In some embodiments, a preferred diameter 310 of the bead 302 may be within a range of about 1.5 mm to about 6 mm. Still other embodiments are possible. In some embodiments, a preferred ratio of the internal diameter 306 of the inlet 312 to that of the chamber 304 ($d_{inlet}/d_{chamber}$) may be within a range of about 0.40 to about 0.66 with a preferred range of 0.46-0.60, and even more preferred range of 0.50-0.60 or 0.53-0.60. In some embodiments, it may be preferred that the length of the chamber 304, $l_{chamber}$, is about 2 times to about 5 times the diameter 310 of the bead 302. In other embodiments, it may be preferred that the length of the chamber 304, $l_{chamber}$, is about 2 to about 3.5 times the diameter 310 of the bead 302. In other embodiments, it may be preferred that the length of the chamber 304, $l_{chamber}$, is about 2 to about 2.5 times the diameter 310 of the bead 302.

In example embodiments, the length of the chamber 304, $l_{chamber}$, may determine whether the actuator 302 freely oscillates, without physical interaction with ends of the chamber 304. Actuator oscillation that frequently impacts the chamber ends may not be desirable as it may generate particulate matter which can inhaled by the patient. In this manner, the length of the chamber 304 may facilitate free oscillation of the actuator 302. A substantially "freely" oscillating actuator 302 may even more effectively disrupt and aerosolize powder agglomerates within the chamber 304, as passed from the source, to provide for more effective deposition of medicament into the lungs of a patient. A substantially "freely" oscillating actuator may include actuators that are able to oscillate to at least some degree in three dimensions.

For example, a study was performed to evaluate the length of the chamber 304 and to determine whether a particular length of chamber 304 would allow the actuator, a spherical bead 302, to "freely" oscillate within the chamber 304. In particular, using a device similar to the tubular body 300, a spherical bead actuator of fixed diameter, about 4 mm, was used across the study. The length of the chamber however was varied as 1.5×, 2.0×, 3.0×, 3.5×, 4.0×, and 9.8× diameter of the bead. In this manner, the study included evaluating at least six different device configurations. In general, it was found that oscillation of the bead within the chamber was similar for lengths up to and including 3.5× diameter of the spherical bead, yet varied for lengths 4.0× and 9.8× diameter of the bead. For example, a similar flow rate through the device was needed to allow the spherical bead to "freely" oscillate within the chamber at least for chamber lengths of 2.0× and 3.0× diameter of the bead. However, a "higher" flow rate was needed to allow the bead to "freely" oscillate within the chamber for a chamber length of 4.0× diameter of the bead. Further the spherical bead did not appear to "freely" oscillate within the chamber for a chamber length of 9.8× diameter of the spherical bead, for any flow rate through the device. At this chamber length, the spherical bead may not be fully influenced by the negative pressure field formed at the inlet of the device by the airflow through the sudden diameter expansion. Other mechanisms may be possible as well.

In another example, a study was performed to evaluate the length of the chamber 304 and to determine whether a particular diameter of the spherical bead actuator 302, for a fixed length of the chamber 304, would allow the actuator 302 to "freely" oscillate within the chamber 304. In particular, using a device similar to the tubular body 300, a chamber of fixed length and diameter, about 10 mm length and about 6 mm diameter, was used across the study. The diameter of the spherical bead however was varied as 3.7 mm, 4 mm, and 4.7 mm. In this manner, the study included evaluating at least three different bead configurations. In general, it was found that oscillation of the bead within the chamber for a 4 mm bead did "freely" oscillate within the chamber at a first particular flow rate. At this flow rate for this device configuration, a distinct audible sound produced by oscillation of the bead within the chamber may be observed. Operation and characteristics of the tubular body 300 having a 4 mm bead diameter is discussed in further detail below.

Further, it was found that oscillation of the spherical bead within the chamber for a 3.7 mm bead did "freely" oscillate within the chamber 304 at or about the first particular flow rate. However, a flow rate greater than the first particular flow rate was needed to observe an audible sound similar to the distinct audible sound produced by oscillation of the spherical bead within the chamber for the 4 mm bead. Here, a greater flow rate may be required to produce the audible sound due to a reduced effective cross-sectional area of the 3.7 mm bead, as compared to the 4 mm bead. Other mechanisms may be possible as well. Further, it was found that oscillation of the bead within the chamber for a 4.7 mm bead did not "freely" oscillate within the chamber at or about the first particular flow rate. Here, the effective cross-sectional area of the 4.7 mm bead may be too large such as to prohibit "free" oscillation within the chamber. Other mechanisms may be possible as well.

As described above, the actuator when oscillating can make an audible sound. The sound resulting from the oscillation of the actuator can be utilized as feedback to the user of the inhaler to confirm they have performed the inhalation maneuver correctly. In general, the volume of sound produced by the oscillating actuator increases with flow, which can encourage the user to perform a deep forceful inhalation. The sound of the actuator is strongly related to the length of the chamber, $l_{chamber}$, and the preferred range is 2.0-3.5× the bead diameter, $d_{bead}$, with 2 to about 2.5× the diameter 310 of the actuator 302 being most preferred.

Figure 4:
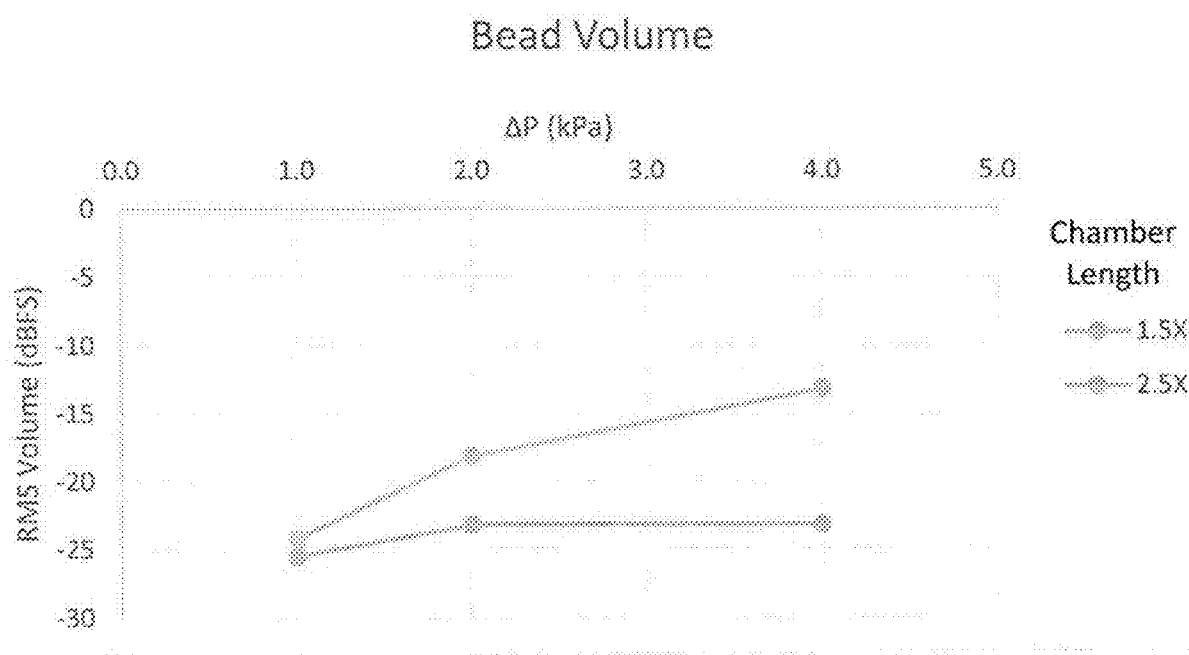
FIG. 4 is a bead sound level plot for different chamber lengths.

Experiments have shown that for chamber lengths less than 2.0× the actuator diameter the actuator oscillates freely but does not produce any significant sound. An experiment was performed to compare the sound from an oscillating bead with a chamber length of 1.5× and 2.5× bead diameter. The chambers for both used $d_{bead}$=4 mm, $d_{inlet}$=2.72 mm $d_{chamber}$=5.89 mm. The sound of 1.5 and 2.5× chamber length was recorded using a microphone and analyzed as shown in FIG. 4. The 2.5× chamber length produced an audible sound from bead oscillation from 1-4 kPa. The audible sound level in general increased with the pressure and flow through the chamber. The 1.5× chamber length showed minimal increase in audible sound from 1-4 kPa compared to the 2.5× chamber length.

Figures 5A, 5B:
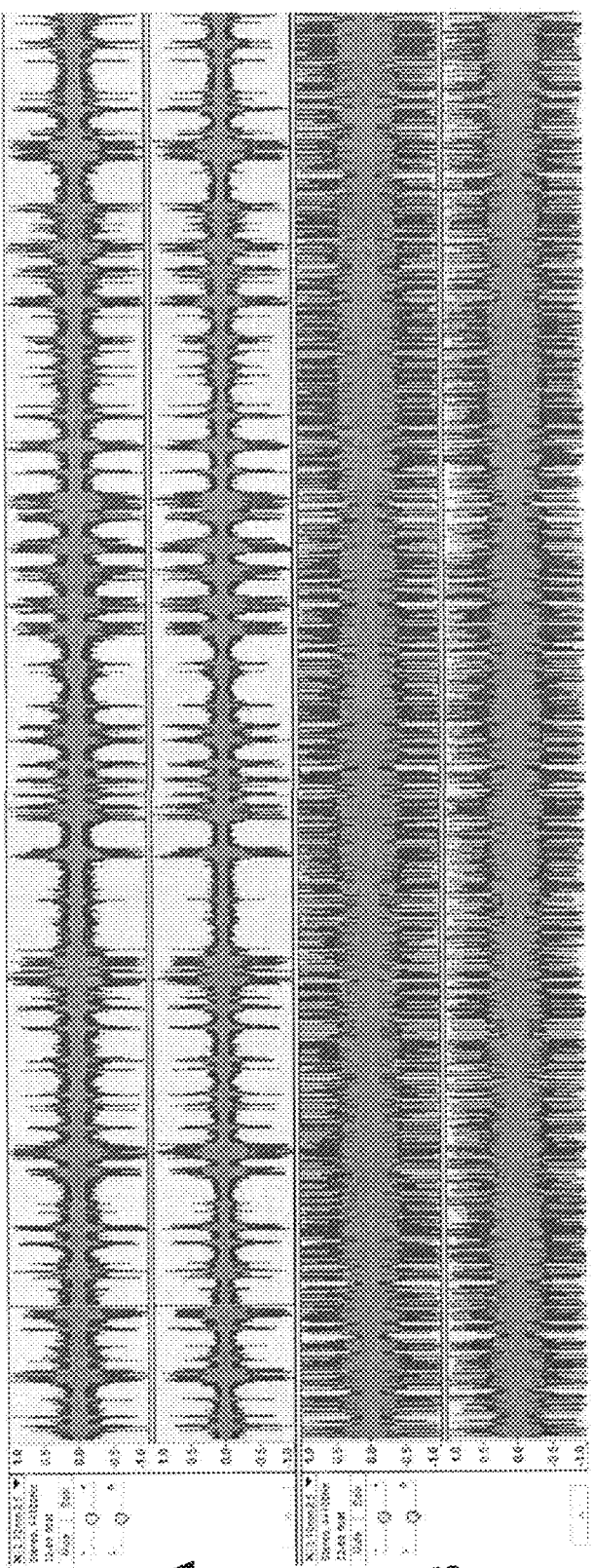
FIG. 5A shows a bead sound comparison for an inlet channel and chamber diameter according to embodiments.
FIG. 5B shows a bead sound comparison for an inlet channel and chamber diameter according to embodiments.
Figure 6A:
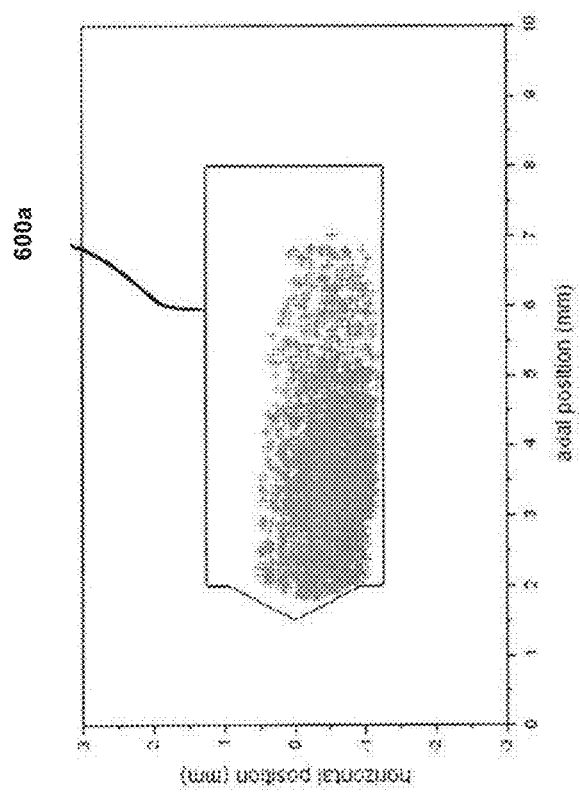
FIG. 6A shows a bead position plot to determine chamber end contact for an inlet diameter of 2.72 mm.
Figure 6B:
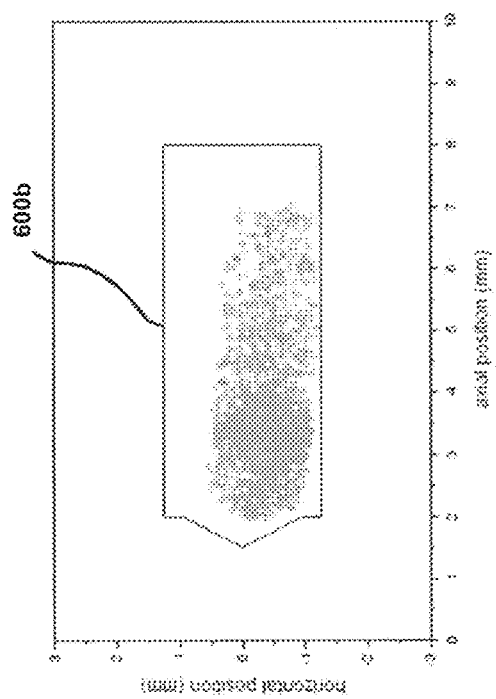
FIG. 6B shows a bead position plot to determine chamber end contact for an inlet diameter of 2.72 mm.
Figure 6C:
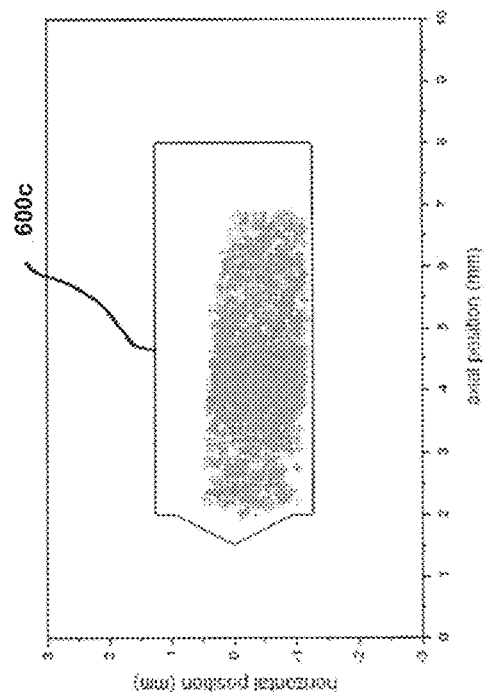
FIG. 6C shows a bead position plot to determine chamber end contact for an inlet diameter of 2.72 mm.
Figure 7A:
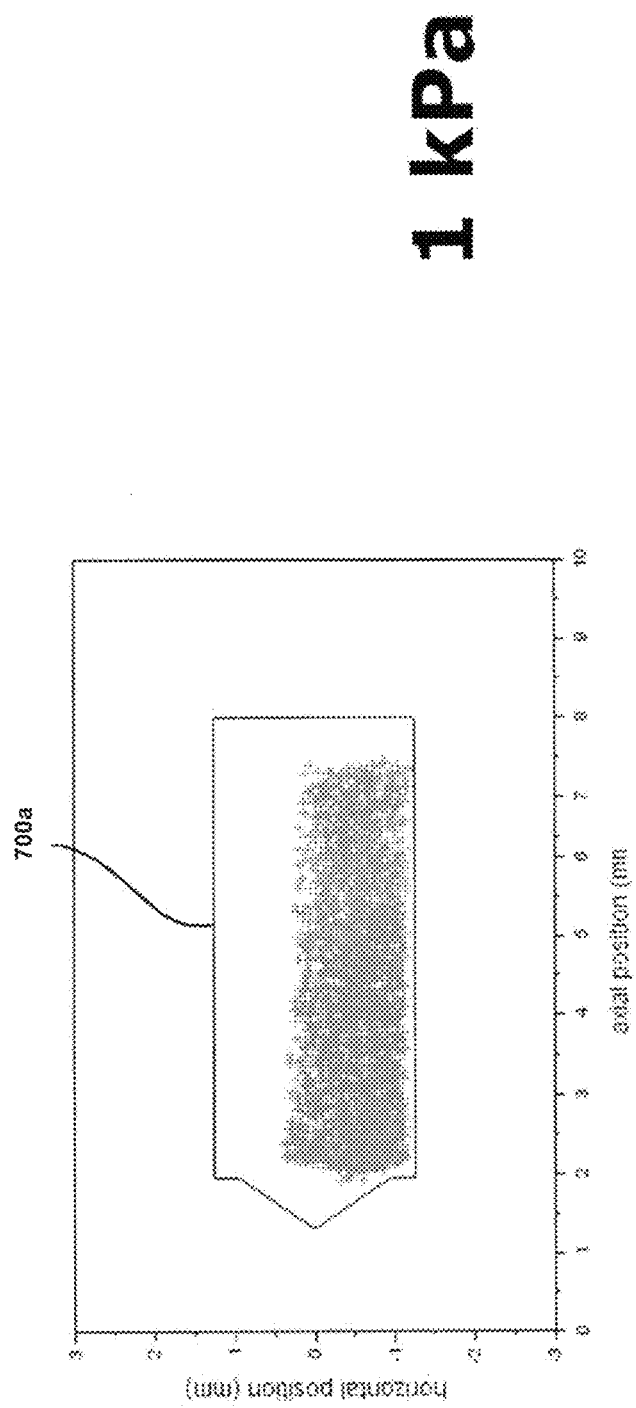
FIG. 7A shows a bead position plot to determine chamber end contact for an inlet diameter of 3.10 mm.
Figure 7B:
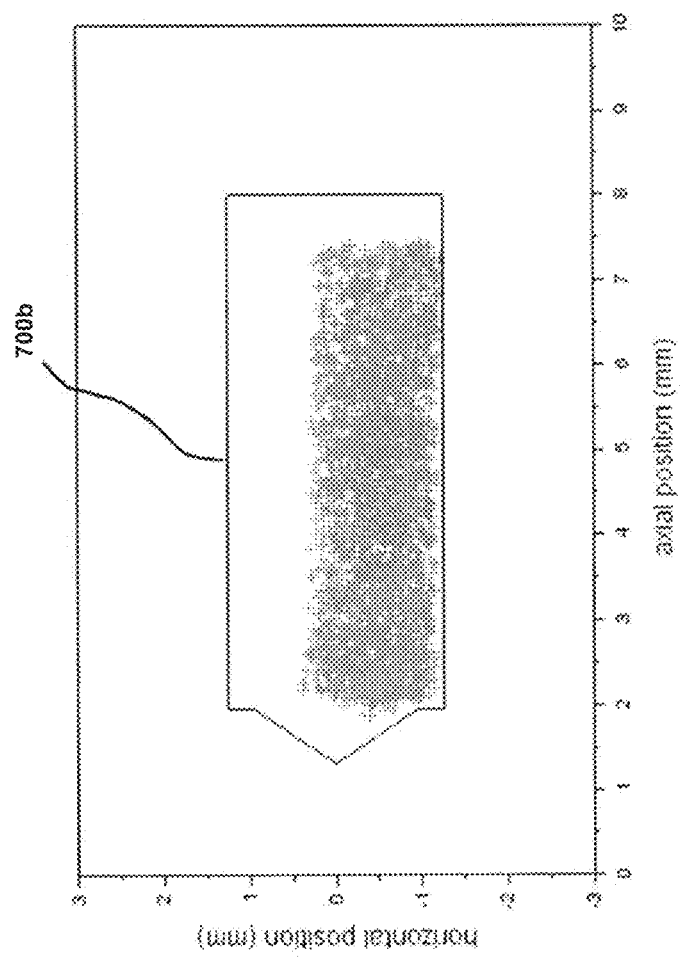
FIG. 7B shows a bead position plot to determine chamber end contact for an inlet diameter of 3.10 mm.
Figure 7C:
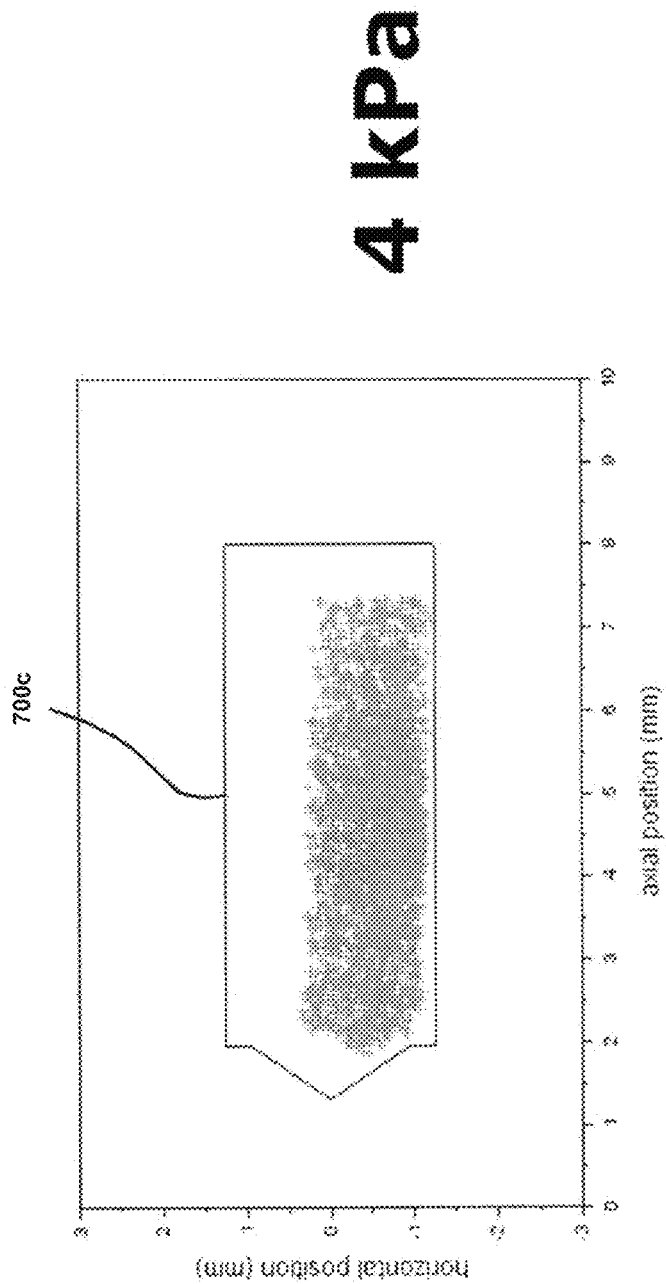
FIG. 7C shows a bead position plot to determine chamber end contact for an inlet diameter of 3.10 mm.

A further experiment was performed to evaluate the sound of a bead using different ($d_{inlet}/d_{chamber}$) ratios. Two chambers were tested with $d_{chamber}$=5.89 mm, and $l_{chamber}$=10 mm, one had an inlet diameter of 2.72 mm and the other 3.10 mm resulting in 0.46 and 0.53 ($d_{inlet}/d_{chamber}$) ratios respectively. The level of the audible sound resulting from the oscillating bead was recorded at 1, 2, and 4 kPa using a microphone. As shown in FIGS. 5A and 5B, the sound profile vs. time over roughly 20 seconds from the larger inlet ($d_{inlet}/d_{chamber}$=0.53) of FIG. 5B was both louder and more consistent at 1, 2, and 4 kPa. The smaller inlet to chamber ratio (0.46) of FIG. 5A showed significant periods of little sound resulting in an intermittent sound. A louder and more consistent sound is desirable for the audio feedback to the user. An intermittent sound such as that exhibited by ($d_{inlet}/d_{chamber}$)=0.46 may provide confusing feedback to the user as the sound is intermittent. The sound from bead oscillation could be used to provide valuable user feedback alerting the user that they have achieved the flow necessary for aerosol delivery. In some embodiments the sound of the bead could be analyzed by a microphone incorporated in the inhaler to determine if the patient reached a minimum flow rate for a period of time. This sound from the microphone could be processed and provide useful information to the patient and train them to achieve the necessary flow rate and time of inhalation for proper use of the inhaler. Furthermore this mechanism could be utilized as a patient compliance monitoring system to report when the inhaler was used and if the patient achieved the flow rate and volume necessary for optimal powder delivery.

Continuing with the above dimensional example and referring again to FIG. 3, the length of the chamber 304 may thus be about 10 mm for a 4 mm diameter bead. In this example, and when the ratio relationship between the diameters of the bead 302, the inlet 312, and the chamber 304 is observed, the bead 302 may oscillate within the chamber 304 generally without experiencing continuous physical collisions with either end of the chamber 304.

An experiment was performed to determine the frequency of bead collision with the ends of the chamber. Two clear chambers were machined from acrylic for use with a 4 mm bead ($d_{chamber}$=5.89 mm, $l_{chamber}$=10 mm, $d_{inlet}$=2.72 mm and 3.10 mm) and the bead motion was recorded at 1200 frames/second for 5 seconds using a high speed camera. The video was analyzed to track the bead through the entire video. The center of the bead was plotted for all frames as seen in FIGS. 6A-C and FIGS. 7A-C. FIGS. 6A-C show pressure drops of 1, 2, and 4 kPa, respectively. FIGS. 7A-C show pressure drops of 1, 2, and 4 kPa, respectively. A polygon (600*a-c* and 700*a-c* in FIGS. 6A-C and FIGS. 7A-C, respectively) was drawn such that if the center of the bead was inside the polygon no contact is made with the ends of the chamber. It was found through high speed video observation bead never made contact with either end of the chamber from 1-4 kPa pressure drop for either inlet size. Such an arrangement may further facilitate development of high energy forces within a chamber, such as chamber 304 of FIG. 3, to more efficiently disrupt and aerosolize medicament powder agglomerates within the chamber 304 for more effective deposition of medicament into the lungs of a patient. Such an arrangement may further facilitate development of high energy forces within the chamber 304 to more efficiently disrupt and aerosolize medicament powder agglomerates within the chamber 304 for more effective deposition of medicament into the lungs of a patient.

In general, high-energy forces may refer to dispersive forces that may strip drug from the bead 302, and deaggregation or deagglomeration forces that may break-up or break-apart aggregates in powder fed into the chamber 304. Here, the terms deaggregation or deagglomeration may be used interchangeably, and the terms aggregation or agglomeration may be used interchangeably. The high-energy forces may be generated by the bead 302 when rapidly oscillating within the chamber 304 via formation of turbulence and eddies within the chamber 304, compression and decompression zones within the chamber 304, and the like. In some instances the bead 302 may be spinning on its axis as well as oscillating along the axial length of the chamber 304. This may more effectively disrupt and aerosolize powder agglomerates within the chamber 304 through the Magnus effect exerted by the spinning bead 302. The Magnus effect is a generation of a sidewise force on a spinning cylindrical or spherical solid immersed in a fluid (liquid or gas) when there is relative motion between the spinning body and the fluid.

When a DPF (Dry Powder Formulation) is passed through the chamber 304 containing the bead 302, which is oscillating "rapidly" such as, for example, at a frequency greater than about 10 Hz, these high frequency oscillations of the bead 302 may produce high-energy forces within the chamber 304. This may disrupt agglomerates of drug particles that may be held together at least by cohesive forces, such as by van der Waals forces, static electrical forces, etc. Additionally, physical collisions between the bead 302, when rapidly oscillating, and potentially aggregated or agglomerated powder particles as they pass through the chamber 304 may promote de-aggregation of the agglomerates. The oscillation frequency may typically be between about 1 to about 1,000 Hz, and may preferably be between about 10 to about 500 Hz, although other frequencies may also occur. However, in some cases, the oscillation frequency could be up to about 2,000 Hz.

As mentioned above, the example bead 302 disposed within the example chamber 304 may oscillate in a manner similar to that described in U.S. application Ser. No. 13/469, 963, filed 11 May 2012, entitled "Bead-Containing Dry Powder Inhaler." However, in accordance with the present disclosure, the bead 302 may not include a pre-coated powder on its surface. Rather, powder may be separately introduced into the chamber 304 from a receptacle or powder storage element (not shown), such as dose containment or dosing chamber which can include but is not limited to capsules, reservoir, and blisters, or other temporary holding compartment or region, or from another dry powder inhaler, as described further below. With this configuration, the powder may be initially placed into a dose containment chamber. When a patient inhales from a mouthpiece, air may be drawn through the dose containment chamber that moves the powder into the chamber 304, where it encounters the bead 302 oscillating primarily along the longitudinal axis L5.

In some embodiments, however, the bead 302 may be coated with drug. This may act as a detachment platform for the drug coated on its surface, as well as a dispersion mechanism for drug formulation located and introduced upstream of the bead 302. For example, for a combination drug product, such as delivering two or more drugs in a single inhalation maneuver, where one drug is delivered in a larger dose, such as an inhaled corticosteroid, than the other drug, such as a long-acting beta-agonist, the lower dose drug may be coated onto the surface of the bead 302, while the larger dose drug is located in a dose containment container, such as a capsule, blister, reservoir, etc., upstream of the chamber 304 containing the drug-coated bead. Thus, during inhalation, oscillation of the bead 302 may serve as a detachment platform to the drug adhered to its surface, and as a dispersion mechanism to the powder that is located upstream.

Additionally, the bead 302 may be coated with a layer of durable material. An example of such a material may include, but is not limited to, gelatin, sugars, any pharmaceutically acceptable film coating materials, including polymers, metallic coatings, anti-static coatings, plasma coatings, etc. This may be beneficial for example when bead material can erode or fragment. In this example, the layer thickness may depend on the density of the material to be added, such that the addition of the coated layer does not eliminate or substantially impair or inhibit the ability of the bead 302 to oscillate within the chamber 304. The bead may have various surface finish ranging from Ra (μm) 0.012-50, where $R_a$ is the average surface roughness. The surface finish may affect bead motion and in turn may improve the dispersion and aerosolization of powder agglomerates within the chamber.

Using the bead 302 as a dispersion mechanism may provide a number of advantages. For example, by employing the oscillating bead in a chamber in the capacity of a dispersion engine, large doses such as, for example, about 1 mg to about 25 mg or greater, may be delivered by delivering them in capsule or blister or reservoir dose containers. However, it will be appreciated that smaller doses may also be delivered. For example, doses greater than about 1 μg of active drug may be delivered. In some cases, the active drug may be blended with a carrier, such as lactose. Also, when the bead 302 is not coated with drug and used as a dispersion mechanism, there is no retention mechanism required to hold the bead 302 tightly within the inhaler, decreasing the complexity of the DPF. Still further, using the bead 302 as a dispersion mechanism may require no additional or complicated processing steps for the DPF formulations, as the powder may be produced by traditionally employed methods, particle engineered formulations may also be used.

Additionally, the bead 302 in the present disclosure may oscillate generally within the center of the chamber 304, along the longitudinal axis L, where physical contact between the bead 302 and inner walls of the chamber 104, and possibly ends of the chamber 304, may occur infrequently, if at all. This type of dispersion mechanism may be beneficial as collisions between walls of the chamber 304 and the bead 302 could serve to rub powder onto either the surface of the bead 302 or inner walls of the chamber 304 when powder is caught there during a physical collision, thereby decreasing an amount of powder available for transfer into the lungs of a patient. Alternatively the frequent collision of the bead 302 with the walls of the chamber 304 may act to scrub off any drug adhered to the wall(s), thus increasing an amount of powder available for transfer into the lungs of a patient.

Alignment of the inlet 312 and the chamber 304 may provide significant advantages over inhalers having an "off-axis" alignment. In particular, the tubular body 300 of the present disclosure may produce an approximately symmetrical flow stream expansion that drives oscillation of the bead 302. Such a configuration may enable a powder dispersion device, or dry powder inhaler, incorporating aspects of the tubular body 300, to be constructed with minimal bulk. For example, the chamber 304 in example embodiments of the present disclosure may be modeled as a cylinder of the dimensions detailed above (e.g., $d_{chamber}$~5.89 mm, $l_{chamber}$~10 mm) for a similar 4 mm bead. Accordingly, a maximum volume occupied by the chamber 304 is about 272 cubic mm based on the expression $v_{cylinder} = \pi r^2 l$.

Referring now to FIGS. 8A and B, simplified, conceptual, example schematic diagrams of the tubular body 300 of FIG. 3 are shown. In particular, the chamber 304 of the tubular body 300 is shown in a series configuration 800 with a second chamber 304 in FIG. 8A, and in a parallel configuration 802 with a second chamber 304 In FIG. 8B. In this example, it is contemplated that multiple drugs in each their own (e.g., two or more) dispersion chambers (e.g., in addition to other elements of the example tubular body 300 as desired) configured in accordance with the principles of the present disclosure may be coupled in series or parallel. Further, it is contemplated that any desired series/parallel combination may also be formed. For example, the series configuration 800 may be coupled in series with the parallel configuration 802. In another example, the parallel configuration 802 may be coupled in series with a single particular chamber 304, and etc.

In addition, it is contemplated that the type and configuration of the bead 302 may vary in the context of FIGS. 8A and B. For example, when multiple ones of the chamber 304 are connected in series and/or parallel, one or more of the respective dispersion chambers may have similar bead sizes, different bead sizes, similar bead materials, different bead materials, and etc. Further, it is contemplated that any desired series/parallel combination may be formed. In general, type and configuration of the bead 302 may vary as desired.

Such an implementation may be beneficial in many respects. For example, for combination therapies, one drug may pass through a particular dispersion chamber and another other drug may pass through a separate dispersion chamber, or both drugs can pass through the same dispersion chamber. Additionally, "downstream" of the dispersion chambers may merge into a single dispersion chamber, or be kept separate throughout the length of the tubular body 300, such that the powders do not mix until they are emitted from the device. Still other benefits and/or advantages are possible as well.

Figure 9:
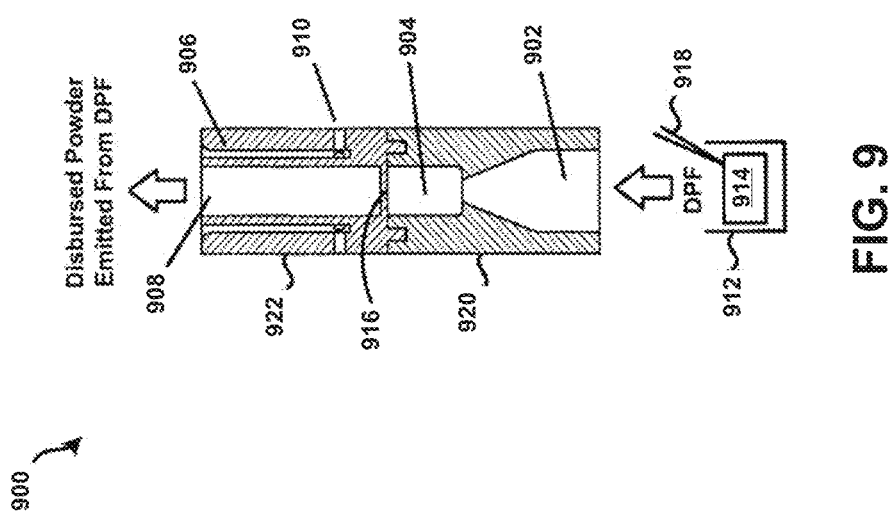
FIG. 9 shows a first view of an example powder dispersion device in cross-section.
Figure 10:
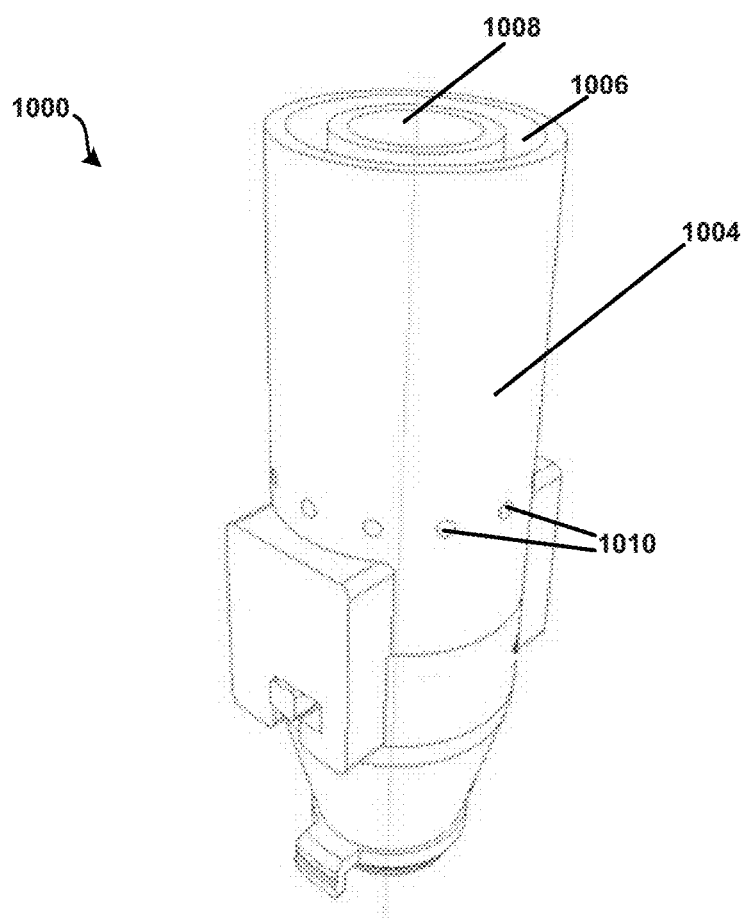
FIG. 10 shows a perspective view of an inhaler device.

Referring now to FIG. 9, an embodiment of a powder dispersion device or inhaler 900 is shown in accordance with the principles of the present disclosure. In particular, FIG. 9 shows the device 900 in cross-section. The device 900 may generally incorporate aspects of the tubular bodies 100, 200, and 400 described above in connection with FIGS. 1, 2A-2C, and 4. Additionally, or alternatively, the device 900 may generally incorporate aspects of one or more of the tubular bodies described below. For example, the device 900 may include a first housing 920 having an inlet 102 and a chamber 904 of the device 900. Additionally, although not expressly shown, an actuator or bead, such as the bead 302 described in FIG. 3, may be positioned within the chamber 904, such as bead 302 is positioned within chamber 304 as shown in FIG. 3. Referring again to FIG. 9, the device 900 may further include a second housing 922 having a sheath flow channel 906 that surrounds and is not in fluid connection with a primary or main powder flow channel 908. In some embodiments, the first housing 920 may be integrally formed with the second housing 922. In one embodiment, the chamber 904 and the main powder flow channel 908 may have at least one common structural dimension, such as internal diameter for example. Additionally, the second housing 922 may itself comprise of, be coupled to, or otherwise incorporated within, a mouthpiece adapted to be placed within the mouth of a patient, or in a nasal adapter adapted to conform to the nostrils of a patient. The device 900 may further include a plurality of flow bypass channels 910 that are formed within the second housing 922. The flow bypass channels 910 may be in fluid connection with the sheath flow channel 906.

The device 900 may further include a dosing chamber 912, a retaining member 916, and a piercing member 918 disposed at an end of the chamber opposite the inlet 902. The piercing member 918 may puncture or otherwise perforate a capsule, blister, or powder reservoir 914 as arranged or positioned within the dosing chamber 912. In general, the retaining member 916 may include at least one opening or aperture sized to permit air and powdered or otherwise aerosolized medicament to pass through the retaining member 916, and to prevent the possibility of the bead (not shown) from exiting the chamber 904. At least one opening or aperture may, in some embodiments, be arranged and configured (e.g., diameter, pattern, symmetry, etc.) to maintain desired air flow characteristics with the device 900, such that the bead may disrupt and aerosolize medicament powder agglomerates within the chamber 904 to provide for more effective deposition of medicament into the lungs of a patient.

In one example, a patient may prime the device 900 by puncturing the capsule, blister, or transfer of a dose from a powder reservoir 914, and then inhale, drawing air through the chamber 904 which in turn draws the DPF from the dosing chamber 912 into the adjacent chamber 904 via the inlet 902, where the bead is rapidly oscillating, creating high-energy forces that may strip drug from the surface of carrier particles in the DPF, or when the bead is drug-covered, and/or de-agglomerate drug powder aggregates and drug-on-drug aggregates. Drug particles may then be deposited in lungs and airways of a patient from the primary or main powder flow channel 908 based on direction of air flow through the device 900. Such a "self-dosing" scenario may be useful for effectively dispensing both traditional binary or ternary DPF formulations, drug and carrier/excipient particles, and pure drug-powder formulations where there are no carrier particles are present. Other embodiments having similar effects are possible, as discussed further below.

In general, the resistance to flow of the device 900 may be adjusted by altering the geometry and/or arrangement of at least one of the inlet 902, the bead, the sheath flow channel 906, the main powder flow channel 908, and the flow bypass channel(s) 910.

FIG. 10 shows a perspective view of a powder dispersion device or inhaler 1000. Inhaler 1000 may correspond to inhaler 900 described above. Additionally, as shown in FIG. 10, the flow bypass channels 1010 may be located radially around the body of a second housing 1004, and fluidly connected to a sheath flow channel 1006. In some embodiments however, the device 1000 may not include any flow bypass channels. In one embodiment, the flow bypass channels 1010 may include a bypass channel where air is drawn into it via multiple individual side holes or channels located radially around the body of the second housing 1004. However, other embodiments are possible. For example, the flow bypass channels 1010 may comprise of different numbers and diameters of individual channels and entry points into the sheath flow channel 1006. Further, one or more of the flow bypass channels 1010 may be parallel through the main powder flow channel 1008, or may be in fluid connection with, and then diverge from, the main powder flow channel 1008. Still other embodiments are possible.

One or more of the bypass channels 1010 may be "opened" or "closed" such as by removal or insertion of a resilient material therein to "unplug" or "plug" the same. This may result in changes in the overall resistance of the device 1000, thereby influencing flow rate through the device 1000. For example, a person may inhale through a "high" resistance inhaler with a lower inspiratory flow rate than they would through a "low" resistance inhaler, despite inhaling with the same inhalation effort. In this manner, the device 1000 may be "tuned" to respond "optimally" to the needs of a patient. In other words, the device 1000 in accordance with the present disclosure may be tailored to suit particular patient needs. For example, resistance of the device 1000 may be approximately inversely proportional to diameter of the bead. Thus, for a "larger" diameter bead, one or more of the flow bypass channels 1010 may be "closed" to increase resistance of the device such that a patient may receive a proper dose of medicament irrespective of possibly diminished inhalation capacity. Further, it is contemplated that the flow bypass channels 1010 when "opened" may at least partially prevent or at least minimize the accumulation or build-up of powder in areas where non-laminar flow, such as flow eddies for example, may be present. Various other possible configurations or arrangements for such housing apertures are described in further detail below.

Figure 11:
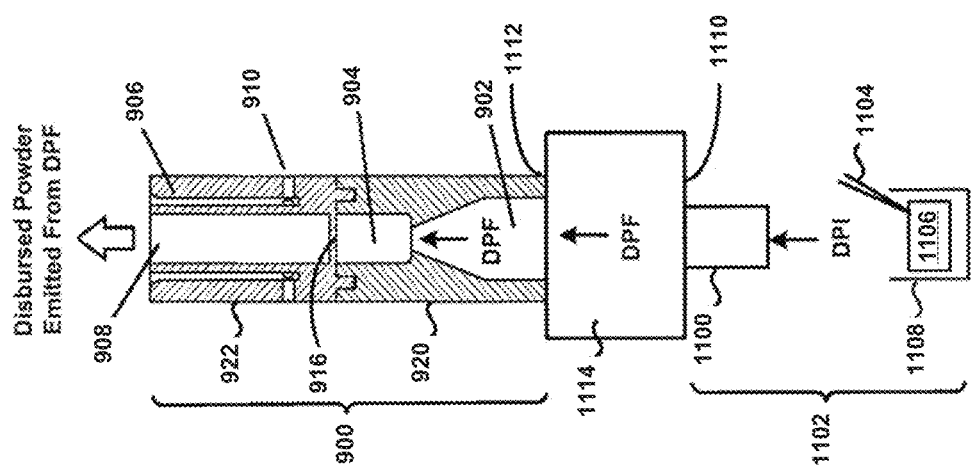
FIG. 11 shows an inhaler device in cross-section.

Referring now to FIG. 11, the device 900 is coupled to a mouthpiece 1100 of an inhaler 1102 by a coupling 1114, thereby allowing powder to flow through the inhaler 1102 as during "normal" operation, and then into the chamber 904 containing a bead (not shown) as described herein. In particular, a piercing member 1104 may puncture or otherwise perforate a DPF containing capsule, blister, or powder reservoir 1106 as contained within a dosing chamber 1108 of the inhaler 1102. Powder may then be caused to flow through the inhaler 1102 into the chamber 904 containing the bead via the mouthpiece 1100 and coupling 1114. The bead may then disrupt and aerosolize DPF powder agglomerates within the chamber 904 to provide for more effective deposition of medicament into the lungs of a patient in a manner such as described above.

In general, the coupling 1114 may be a rigid or flexible coupling formed of any material, or combination thereof, such as thermoplastic/thermosetting plastics, metals, glasses, elastomers, etc., and may be coupled to the mouthpiece 1100 of the inhaler 1102 on a first end 1110, and to the device 900 on a second end 1112. Here, it may be preferred that the material has surface properties that minimize the attraction of powder particles. The coupling 1114 may be permanently fastened to, such as being integrally formed therewith, at least one of the inhaler 1102 and the device 900, or may be removable fastened with least one of the inhaler 1102 and the device 900. For example, the coupling 1114 may be fastened to the inhaler 1102 by one of a "snap-fit" or a "pressure-fit" or a "twist-to-fit" mechanism, etc., such as in a "quick" connect/disconnect implementation. Still other embodiments are possible. For example, it will be appreciated that the device 900 may not be limited to being "clipped" or otherwise "coupled" to other inhalers. Further, aspects of the present disclosure may be used in combination with any type of DPF dose containment system, and may not be limited to a capsule, blister, or reservoir dose containment systems.

As discussed above in connection with FIG. 9, a patient may prime the device 900 by puncturing the capsule, blister, or powder reservoir 914, and then inhale, drawing the powder from the dosing chamber 912 into the adjacent chamber 904 via the inlet 902, where the bead is rapidly oscillating, creating high-energy forces that may strip drug from the surface of carrier particles (e.g., when the bead is drug-covered), and/or de-agglomerate powder aggregates. Drug particles may then be deposited in lungs and airways of a patient from the primary or main powder flow channel 908 based on direction of air flow through the device such as shown in FIG. 9. Such a "self-dosing" scenario may at least be useful for effectively dispensing both traditional binary or ternary DPF formulations, drug and carrier/excipient particles, and pure drug-powder formulations where there are no carrier particles are present. Other embodiments are however possible.

Figure 12:
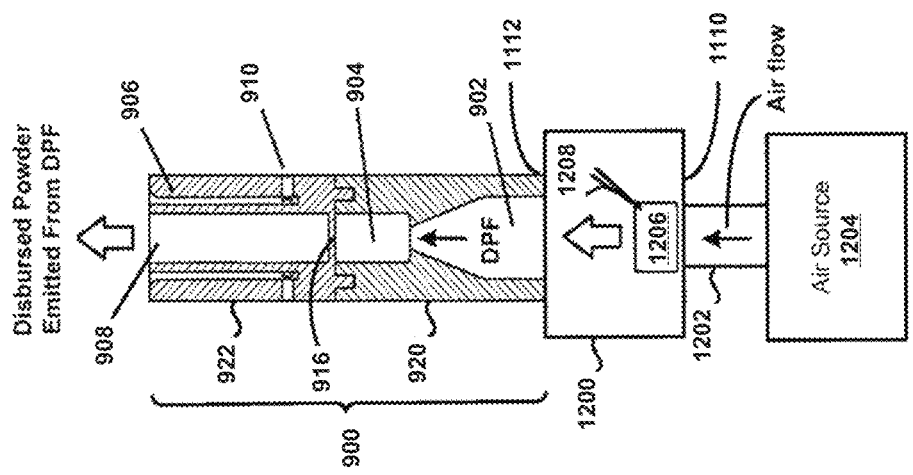
FIG. 12 shows an inhaler device in cross-section.

For example, referring now specifically to FIG. 12, a "forced-dosing" scenario is described in accordance with the present disclosure and the device 900. In this example, a coupling 1200 is shown that is removably coupled to the first housing 920 of the device 900. The coupling 1200 includes an inlet 1202 that is removably coupled to an air source 1204. In one embodiment, an individual other than a patient may prime the device 900 by puncturing a capsule, blister, or reservoir 1206 of the coupling 1200 using a piercing member 1208. The source 1204 may then be employed to force air through the device 900, drawing powder from the reservoir 1206 into the adjacent chamber 904 via the inlet 902, where the bead is rapidly oscillating, creating high-energy forces that may strip drug from the surface of carrier particles (e.g., when the bead is drug-covered), and/or de-agglomerate powder aggregates. Drug particles may then be deposited in lungs and airways of the patient from the primary or main powder flow channel 908 based on direction of air flow through the device 900.

Such a "forced-dosing" scenario may beneficial when, for example, emergency treatment of unconscious or otherwise unresponsive personnel or patients may be necessary. For example, the device 900 may enable a responder to administer treatment agent to the lungs of a patient. Additionally, the second housing 922 may itself comprise of, be coupled to, or otherwise incorporated within, a mouthpiece adapted to be placed within the mouth of a patient, or in a nasal adapter adapted to conform to the nostrils of a patient. In the example of FIG. 12, the second housing 922 of the device 900 may be securely positioned within or on the mouth or nasal passages of a patient. With air expelled from the lungs of a responder into the inlet 1202, the device 900 may be activated or actuated such as to deposit a treatment agent into the lungs and airways of the patient. In this example, the source 1204 corresponds to the lungs of an individual. Other embodiments are possible. For example, in some embodiments the source 1204 may comprise of a ventilation bag, mechanical ventilator, mechanical pump, etc. Still other embodiments are possible.

Figure 13:
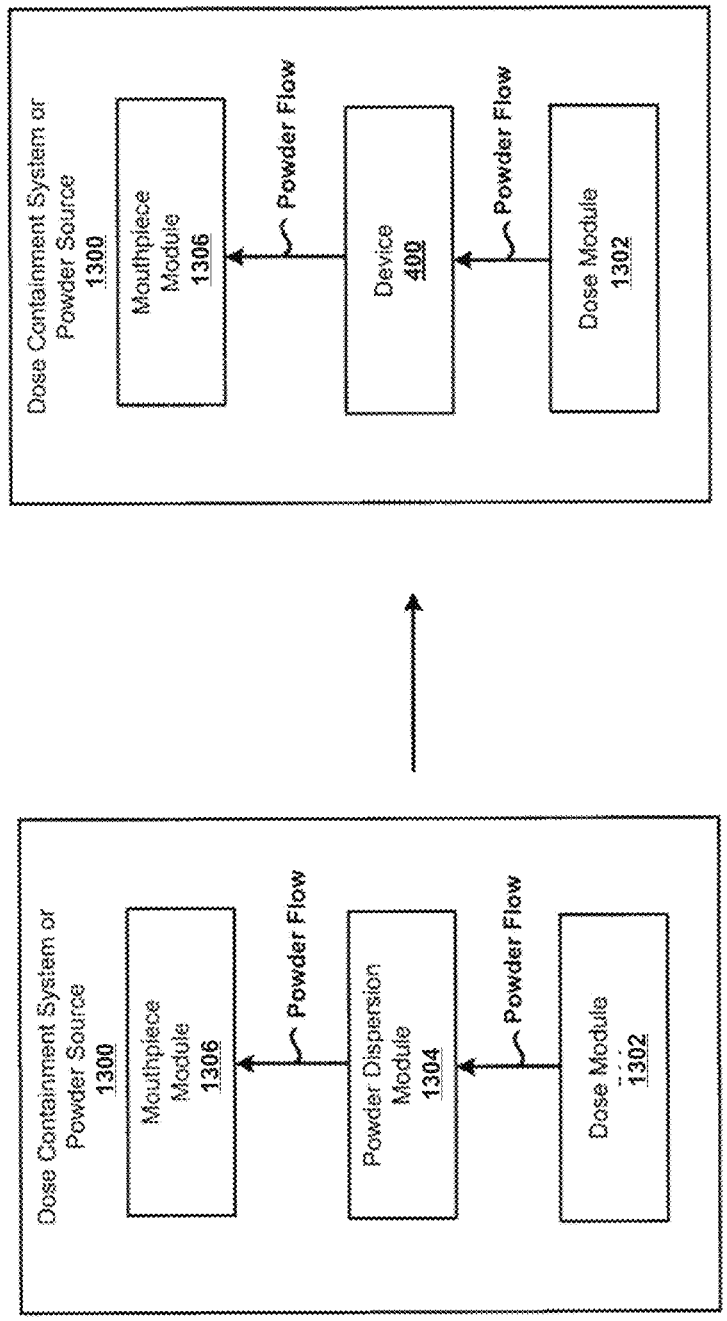
FIG. 13 shows an inhaler device incorporated into an existing inhaler system.

At least FIG. 13 illustrates a scenario in which the device 900 is coupled to, or fitted onto, an external feature of a dose containment system or powder source. Other embodiments are however possible. For example, referring now to FIG.

13, a scenario is illustrated in which a device, such as device 900 described herein, is coupled to, or fitted onto, an internal feature of a dose containment system or powder source. In particular, the device may replace a powder dispersion mechanism internal to an existing inhaler. An example of an existing inhaler may include the HandiHaler®, Twisthaler®, Turbuhaler®, Novolizer®, Plastiape RS01®, Turbospin® dry powder inhalers and others. Other embodiments are possible.

For example, a typical dose containment system or powder source 1300 may generally include a dose module 1302 that holds a portion of DPF, a powder dispersion module 1304, and a mouthpiece module 1306 that would in practice be used to deliver a dose of the DPF to a patient. In general, the powder dispersion module 1304 may exhibit a tortuous path the DPF needs to navigate between its introduction into the flow path and release from the mouthpiece module 1306. The tortuous path may possibly deaggregate DPF aggregates to some degree, but may also add flow resistance. In accordance with the principles of the present disclosure, the dose containment system or powder source 1300 may be modified to replace the powder dispersion module 1304 with the device, or subassemblies of the device, including an inlet, chamber with a bead, and an outlet similar to the device. Further, this may or may not include the second housing of the device, where an existing element of an inhaler being modified may instead be used. In this example, the device may enhance the efficiency of de-aggregation of DPF of the dose containment system or powder source 1300, and may lower the resistance to flow within the dose containment system or powder source 1300. Other benefits and advantages are possible as well.

Figure 14:
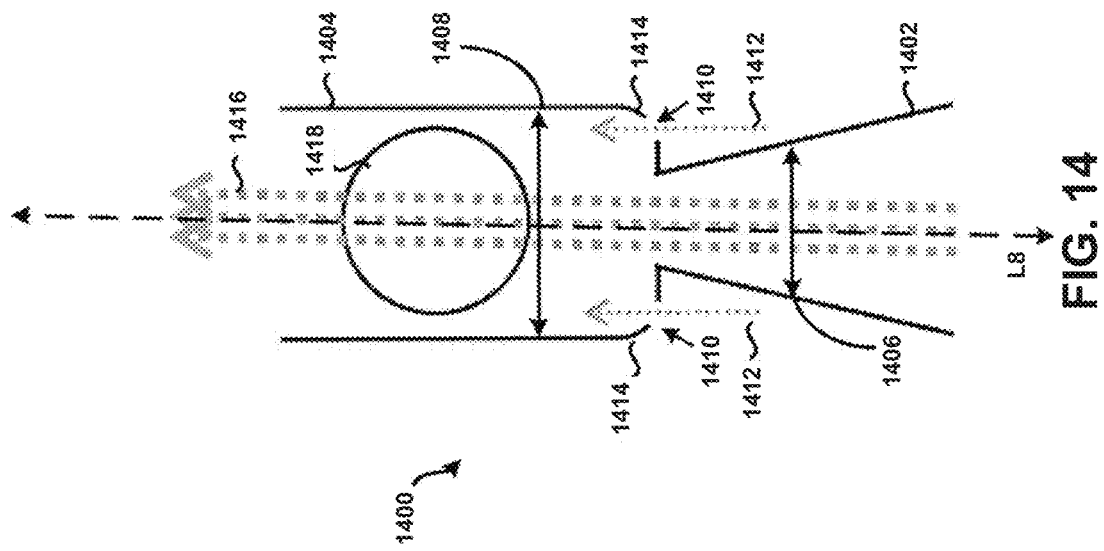
FIG. 14 shows a cross-section of a second example tubular body.

Referring now to FIG. 14, a cross-section of an embodiment of a tubular body 1400 having an inlet 1402 and an actuator 1418 in a dispersion chamber 1404 is shown according to the principles of the present disclosure. In many aspects, the second example tubular body 1400 is similar to at least the tubular body 100 of FIG. 1. For example, a fluid flow path of the inlet 1402 is defined by a first internal diameter 1406 that varies or tapers along a longitudinal axis L8, and a fluid flow path of the dispersion chamber 1404 is defined by a second internal diameter 1408. Further, one or more apertures 1410 are formed within the tubular body 1400 at particular locations to allow a secondary supply of air or air flow 1412 (sometimes referred to as "chase air") to enter the tubular body 1400 during its use, to prevent or at least minimize the unintended accumulation or build-up of powder within the tubular body 1400. In particular, it will be appreciated that air flowing through the one or more apertures 1410 may advantageously prevent or at least minimize the unintended accumulation or build-up of powder within internal edges or corners 1414 of the tubular body 1400 that are substantially adjacent the inlet 1402, because the force of that air would push powder away from the corners 1414 into the primary air stream 1416 for subsequent deposition into the lungs of a patient in a manner similar to that as discussed above. Among other things, this may advantageously increase the efficiency of powder deposition into the lungs of a patient, prevent build-up of powder that can dislodge in subsequent uses of the chamber as a multi-dose inhaler device resulting in a super-dose to be delivered to the patient, and/or prevent undesired waste of powder.

Figure 15:
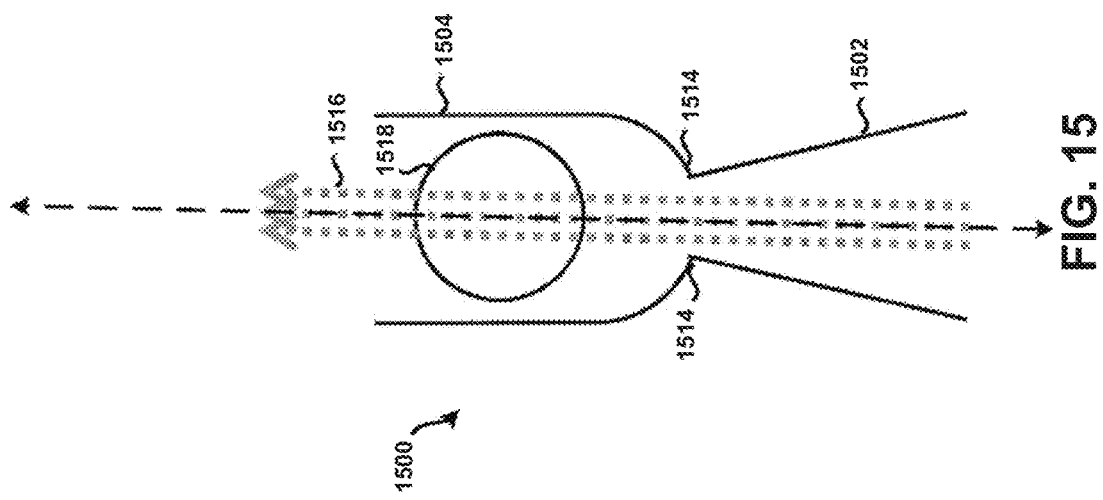
FIG. 15 shows a cross-section of a sixth example tubular body.
Figure 16:
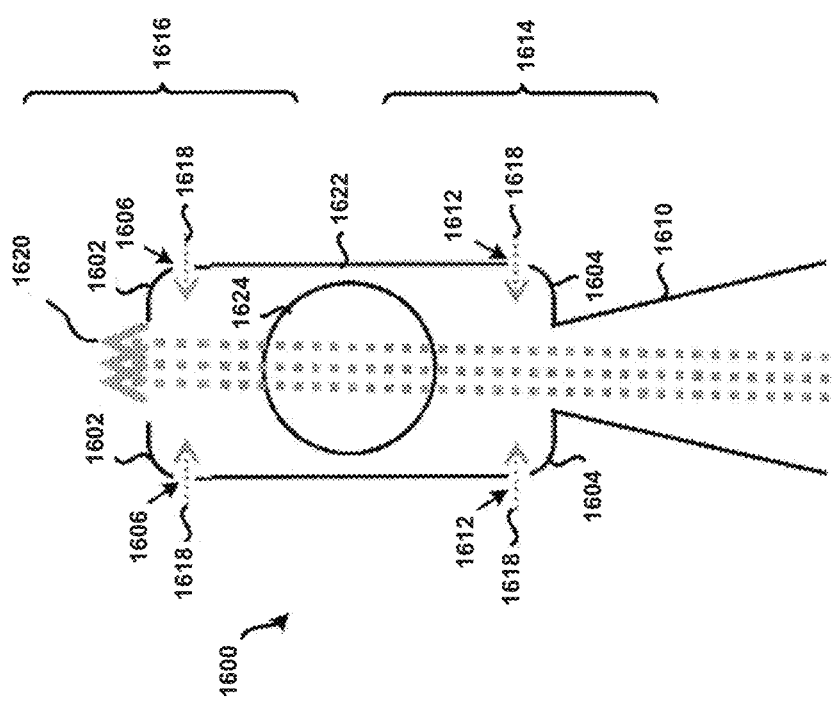
FIG. 16 shows a cross-section of a seventh example tubular body.
Figure 17:
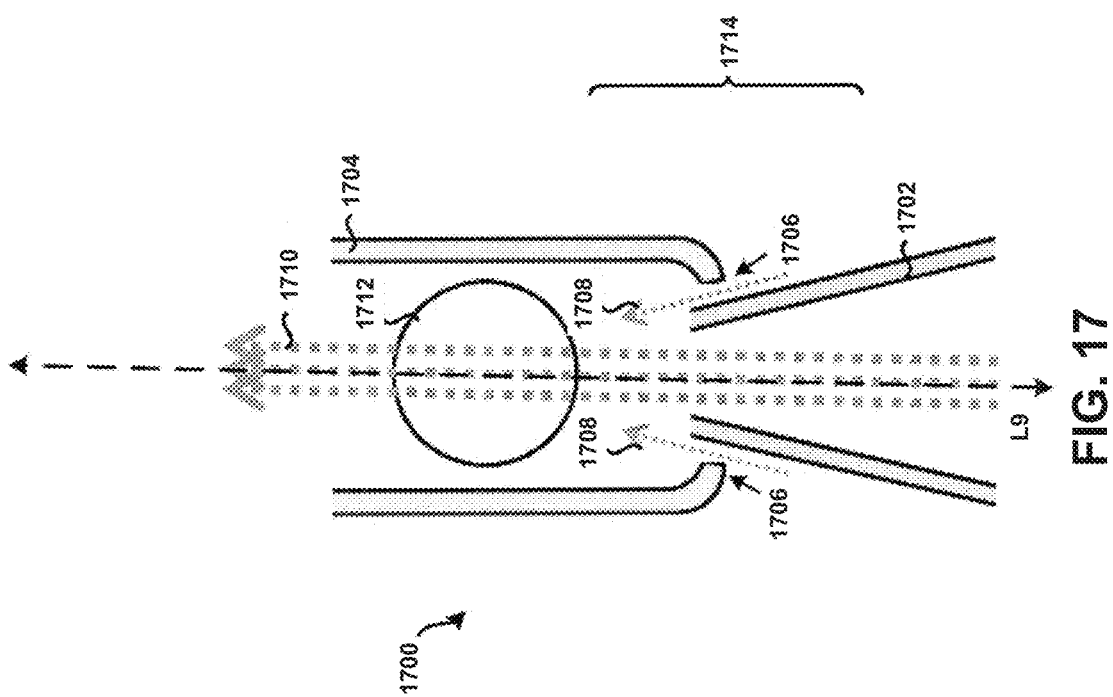
FIG. 17 shows a cross-section of a fourth example tubular body.

Additionally, or alternatively, the corners 1414 of the tubular body 1400 may be formed to exhibit rounded or curved surfaces to prevent or at least minimize the unintended accumulation or build-up of powder within the tubular body 1400. FIG. 15 in particular shows corners 1514 of a tubular body 1500, which may correspond to tubular body 1400, formed to exhibit rounded or curved surfaces, without any apertures. Tubular body 1500 may include an inlet 1502, dispersion chamber 1504, primary air stream 1516, and actuator 1518 similar to the features described in relation to FIG. 14. Other embodiments are possible. For example, FIG. 16 in particular shows corners 1602 of a tubular body 1600 that are formed to exhibit rounded or curved surfaces on an end of the tubular body 1600 opposite corners 1604. Tubular body 1600 may correspond to tubular body 1400 and include similar features, such as dispersion chamber 1622 and an actuator 1624. Further, apertures 1606 are formed within the tubular body 1600 near or adjacent the corners 1602. It is contemplated that any feature or element discussed as being near or adjacent an inlet 1610 may additionally, or alternatively, be formed on an end of the tubular body 1600 opposite of the inlet 1610. This principle is applicable to each respective tubular body discussed in the context of the present disclosure. Further, the configuration and particular geometry of the corners 1602 and/or the apertures 1606 need not necessarily be the same as that exhibited by the corners 1604 and/or apertures 1612. Apertures 1606 and 1612 may allow a secondary airflow 1618 that prevents or at least minimizes the unintended accumulation or build-up of powder within internal edges or corners 1602 and 1604 of the tubular body 1600 that are substantially adjacent the inlet 1610, because the force of that air would push powder away from the corners 1602 and 1604 into the primary air stream 1620 for subsequent deposition into the lungs of a patient in a manner similar to that as discussed above. For example, the tubular body 1600 may have a first portion 1614 configured similar to first portion 1714 shown in FIG. 17, whereas a second portion 1616 may be configured as shown in FIG. 16. Still many other embodiments are possible.

It will be appreciated that such rounded or curved surfaces may more effectively prevent powder from accumulating or adhering to portions of the corners 1604 when compared to other profiles that have a sharp transition between surfaces, such as the stepped-edge profile shown in FIG. 1. In addition to providing desirable fluid flow characteristics, one or both of the apertures 1612 and the rounded corners 1604 may further facilitate efficient and effective fabrication of the tubular body 1600 by injection molding for example.

In the example of FIG. 14, the secondary air flow 1412 comprises air flowing through the apertures 1410 and into the dispersion chamber 1404 in a substantially or approximately parallel direction to the primary air stream 1416. Many other embodiments are possible. For example, referring now to FIG. 18, a cross-section of an embodiment of a tubular body 1800 is shown. Tubular body 1800 may correspond to tubular body 1400 and include similar features including an actuator 1812. Apertures 1804 are formed such that the secondary air flow 1806 comprises air flowing through the one or more apertures 1804 and into a dispersion chamber 1802 in a substantially or approximately perpendicular direction to the primary air stream 1810. The benefits associated with the secondary air flow 1806 are similar to that described above in connection with FIG. 14.

Figure 18:
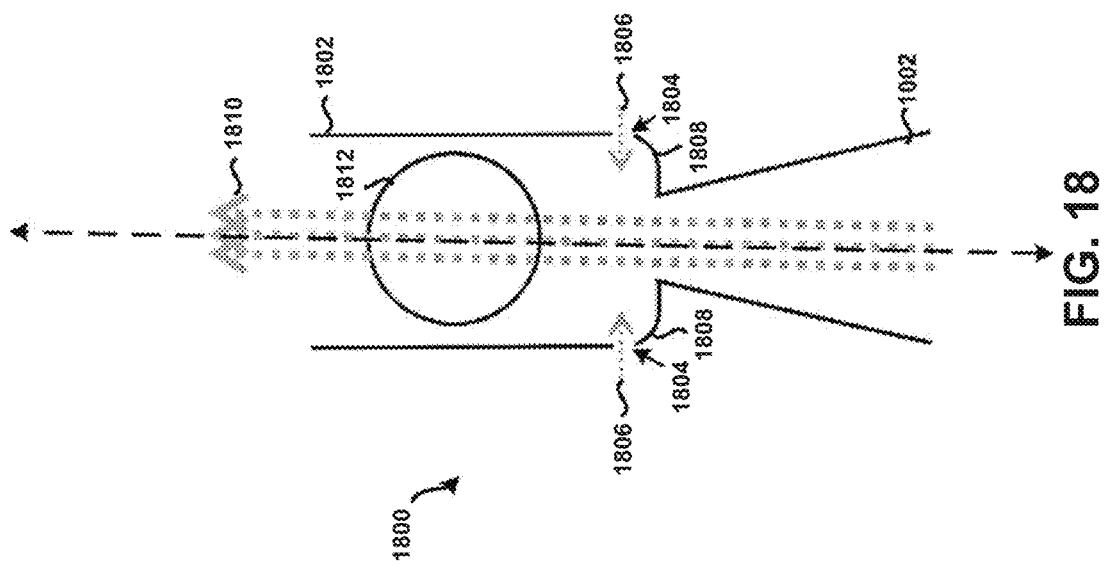
FIG. 18 shows a cross-section of a third example tubular body.

Further, it is contemplated that the tubular body 1800 may be fabricated to exhibit the arrangement or configuration of the apertures 1410 as shown in FIG. 14 together with the arrangement or configuration of the apertures 1804 as shown in FIG. 18. In either case, that is, in scenarios where the tubular body 1800 is fabricated to incorporated the apertures 1410 and/or 1804 as shown in FIG. 14 or FIG. 18, or where the tubular body 1800 is fabricated to incorporate the apertures 1410 and/or 1804 as shown in both FIG. 14 and FIG. 18, it is contemplated that the diameter of the apertures 1410 and/or 1804 (i.e., when circular, however, other polygonal apertures are contemplated) in addition to the spatial arrangement of the apertures 1410 and/or 1804 may be defined so that the desired fluid flow characteristics of the tubular body 1800 are realized. For example, the apertures 1410 and/or 1804 may be defined within the tubular body 1800 so as to exhibit a specific pattern or symmetry that facilitates deposition of powder into the lungs of a patient, in tandem with preventing or at least minimizing the accumulation or build-up of powder in or near the corners 1808 of the tubular body 1800. Further, it is contemplated that the apertures 1410 and/or 1804 may be formed or defined by means other than an injection molding technique for example.

For example, referring again to FIG. 17, an embodiment of a tubular body 1700 is shown whereby a body of the inlet 1702 and a body of a dispersion chamber 1704 are not integral, but rather are separate pieces so that apertures 1706 are formed by a gap(s) between the body of the inlet 1702 and the body of the dispersion chamber 1704, when those two pieces are generally coupled together. In this example, the apertures 1706 are formed such that the secondary air flow 1708 comprises air flowing through the apertures 1706 and into the dispersion chamber 1704 in a substantially or approximately off-axis direction in reference to a primary air stream 1710 and/or the longitudinal axis L9. It is contemplated that such a multi-piece arrangement or configuration may take many different forms, where a particular multi-piece arrangement or configuration may be implementation-specific, and/or possibly fabrication-method-specific, and so thus may evolve as requirements or specifications, and possibly fabrication technologies or techniques, evolve. Dispersion chamber 1704 may house an actuator 1712.

Figure 19:
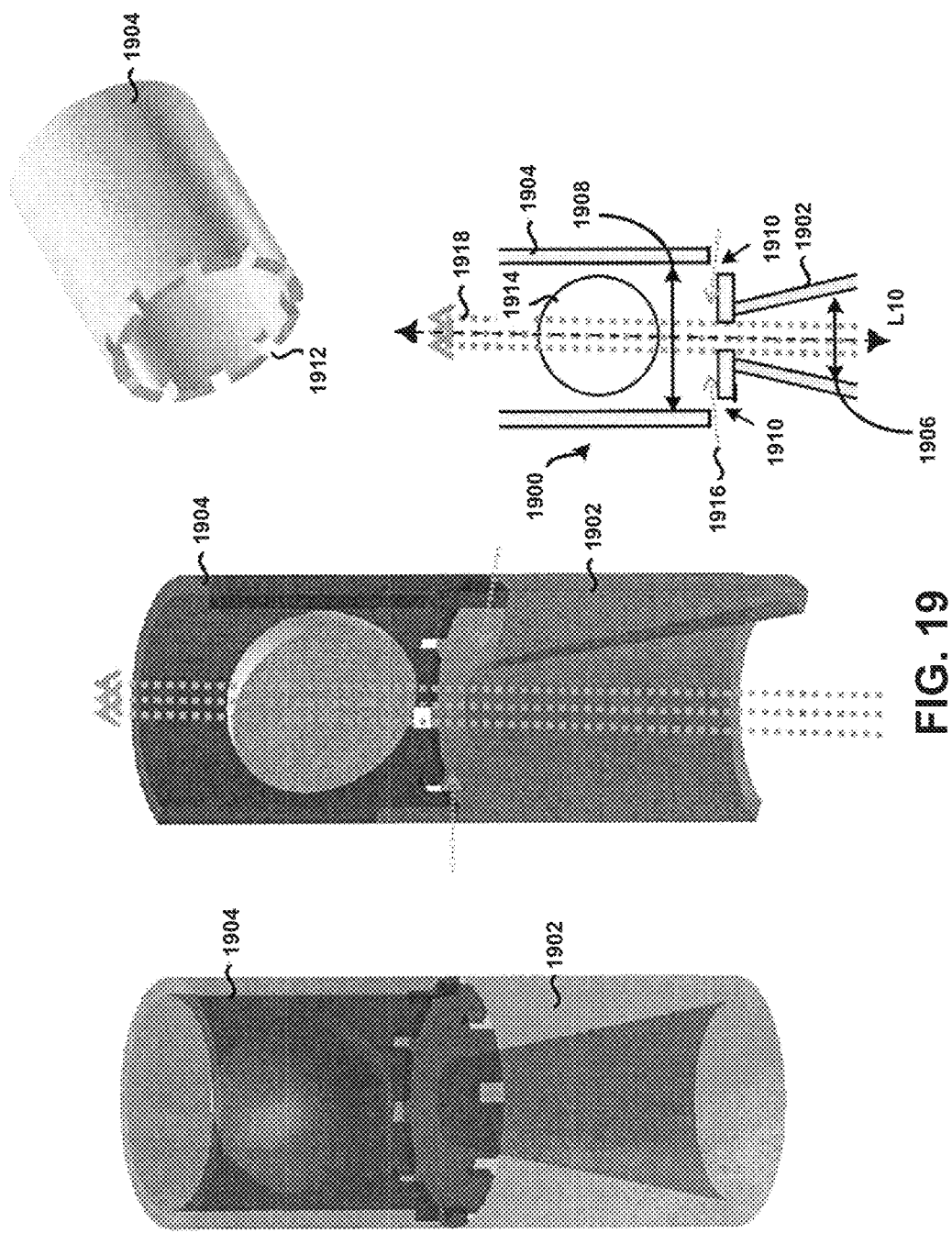
FIG. 19 shows a cross-section of a fifth example tubular body.

For example, referring now to FIG. 19, an embodiment of a tubular body 1900 having an inlet 1902 and a dispersion chamber 1904 is shown according to the principles of the present disclosure. In many aspects, the tubular body 1900 is similar to at least the tubular body 1400 of FIG. 14. For example, a fluid flow path of the inlet 1902 is defined by an internal diameter 1906 that varies or tapers along a longitudinal axis L10, and a fluid flow path of the dispersion chamber 1904 is defined by an internal diameter 1908. Further, the body of the inlet 1902 and the body of the dispersion chamber 1904 are not integral, but rather are separate pieces so that one or more apertures 1910 are formed by a gap(s) between the body of the inlet 1902 and the body of the dispersion chamber 1904 when those two pieces are generally coupled together. More specifically, the dispersion chamber 1904 is formed to exhibit notches 1912, and when the body of the inlet 1902 and the body of the dispersion chamber 1904 are generally coupled, the apertures 1910 are formed as gaps between the body of the inlet 1902 and the body of the dispersion chamber 1904. In general, it is contemplated that the notches 1912 may be defined as desired so that the apertures 1910 exhibit a specific shape, pattern, and/or symmetry that facilitates deposition of powder into the lungs of a patient, in tandem with preventing or at least minimizing the accumulation or build-up of powder in or near internal surfaces of the mated assembly, and in particular the dispersion chamber 1904 and actuator 1914. Apertures 1910 are formed such that secondary air flow 1916 comprises air flowing through the one or more apertures 1910 and into dispersion chamber 1904 in a substantially or approximately perpendicular direction to a primary air stream 1918. The benefits associated with the secondary air flow 1916 are similar to that described above in connection with FIG. 14.

The features or aspects of the present disclosure may be beneficial and/or advantageous in many respects. For example, to help minimize the buildup or accumulation of powder within at least the above-described dispersion chambers, it is contemplated that the outside corners of the inlet surface of the chamber may be formed so that "small" amounts of air are allowed to flow into the outermost corner via a gap/holes at the outermost edge of the inlet surface and the chamber cylinder. The dimension of the gap or gaps may be critical so as to allow sufficient air to flow into the outermost corner to minimize or prevent powder buildup, essentially sweeping away or causing the powder trapped there by the eddies not to build up in the first place. The flow though still is low enough not to alter the linear oscillation characteristics of the bead, and the negative pressure field that is present in the chamber that draws the bead back toward the inlet when air flows into the main inlet to the chamber, and is above the level needed to make the bead oscillate. The "corner air flow" can be via holes in the corner, or via a designed-in gap caused by the design of the mating parts that make up the cylinder. It is contemplated that less than about 25% of the main flow, less than about 10% of the main, less than about 5% of the main flow, or less about than about 1% of the main flow may prevent powder buildup in the corners, depending on the characteristics of the powder deposited in the corners and the physical properties and components thereof.

Figure 20:
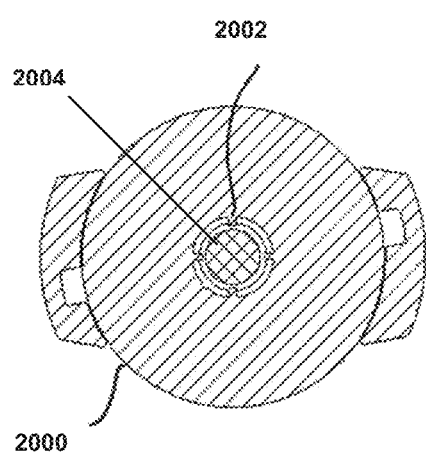
FIG. 20 shows one embodiment of chamber ribs.
Figure 21:
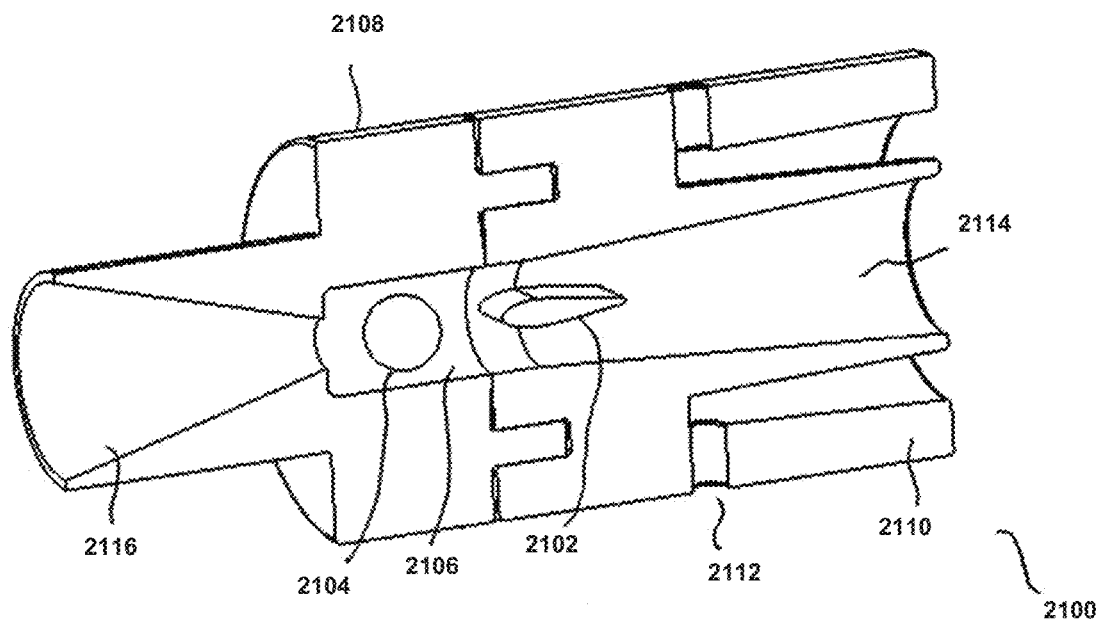
FIG. 21 shows one embodiments of bead retention features.
Figure 22:
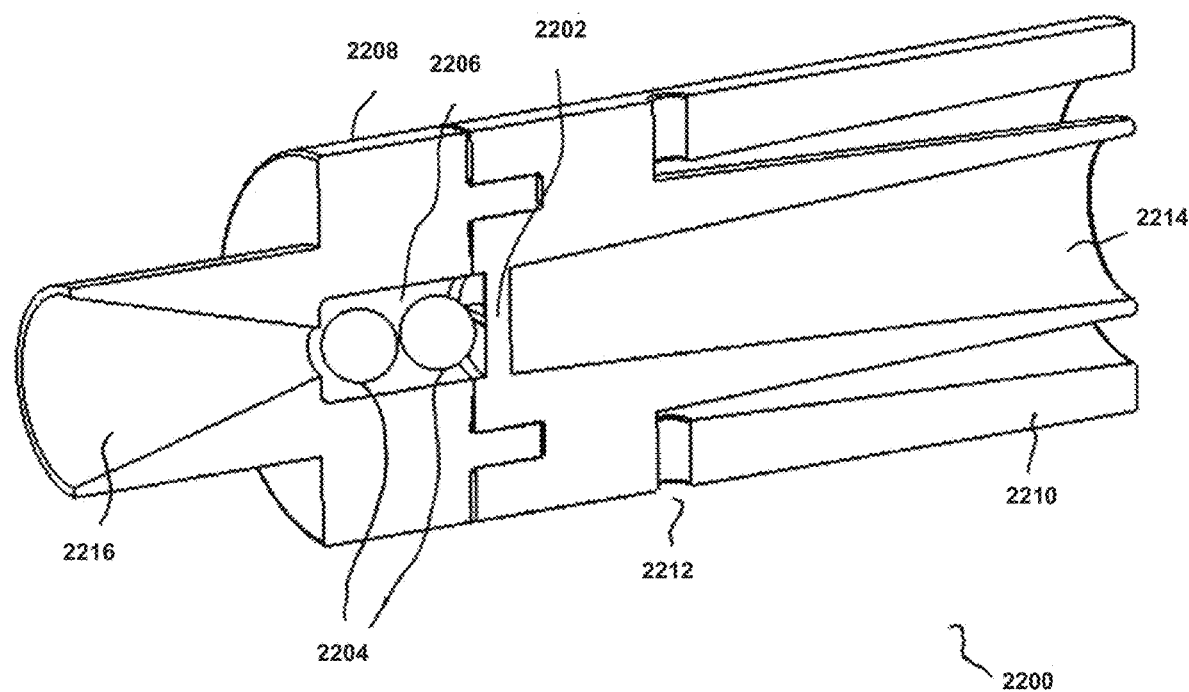
FIG. 22 shows an embodiment having two beads in a chamber.

Additional features could further improve the disruption and dispersion of powder agglomerates within the chamber by the bead. The additional features may include one or more ribs 2002 in a chamber 2004 of inhaler 2000 as shown in FIG. 20 that would restrict the circumferential movement of the bead limiting a bead to axial movements. This may increase the speed and frequency of the bead oscillation in the chamber 2004. In addition, a retention feature 2102 that keeps a bead 2104 from exiting a chamber 2106 of an inhaler 2100 could be constructed from a wing as shown in cross section in FIG. 21. The wing as a retention feature 2102 could have several benefits to the design such as lowering inhaler resistance and increasing bead speed and or frequency among other possible benefits Inhaler 2100 may also include an inlet 2116, a first housing 2108, a second housing 2110, apertures 2112, and a main powder flow channel 2114, such as those described above. In some embodiments, two or more beads 2204 may be placed in a single chamber 2202 of an inhaler 2200 as shown in FIG. 22, this may improve the disruption and dispersion of powder agglomerates within the chamber. Inhaler 2200 may also include a dispersion chamber 2206, an inlet 2216, a first housing 2208, a second housing 2210, apertures 2212, and a main powder flow channel 2214, such as those described above Inhalers 2000, 2100, and/or 2200 may all include tubular bodies as described herein, such as tubular bodies that correspond to tubular bodies 100, 200, 300, 1400, 1500, 1600, 1700, 1800, and 1900 described herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It will be appreciated that various combinations of features described herein may be utilized. For example, features not discussed or shown together may be combined in accordance with embodiments of the invention, while other embodiments may include additional features and/or may omit one or more features disclosed herein.

Figure 23:
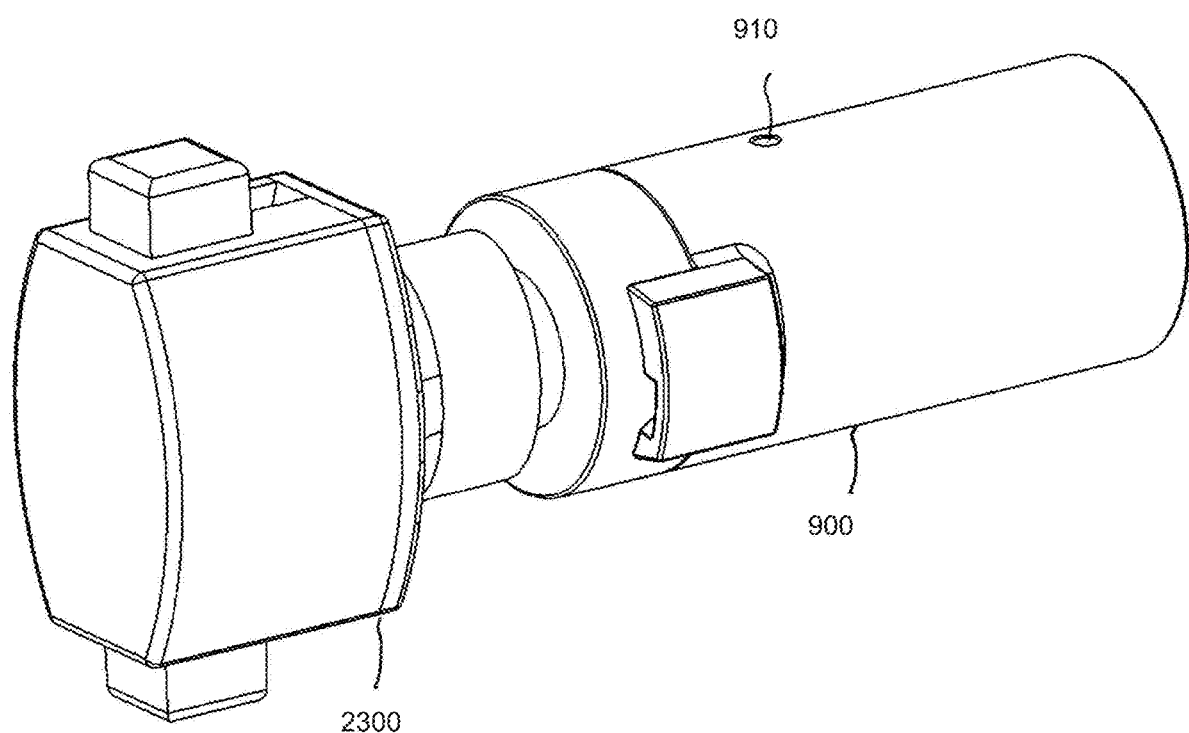
FIG. 23 shows an embodiment of a DPI with capsule piercing and powder feed element from a Plastiape RS01 inhaler.
Figure 24:
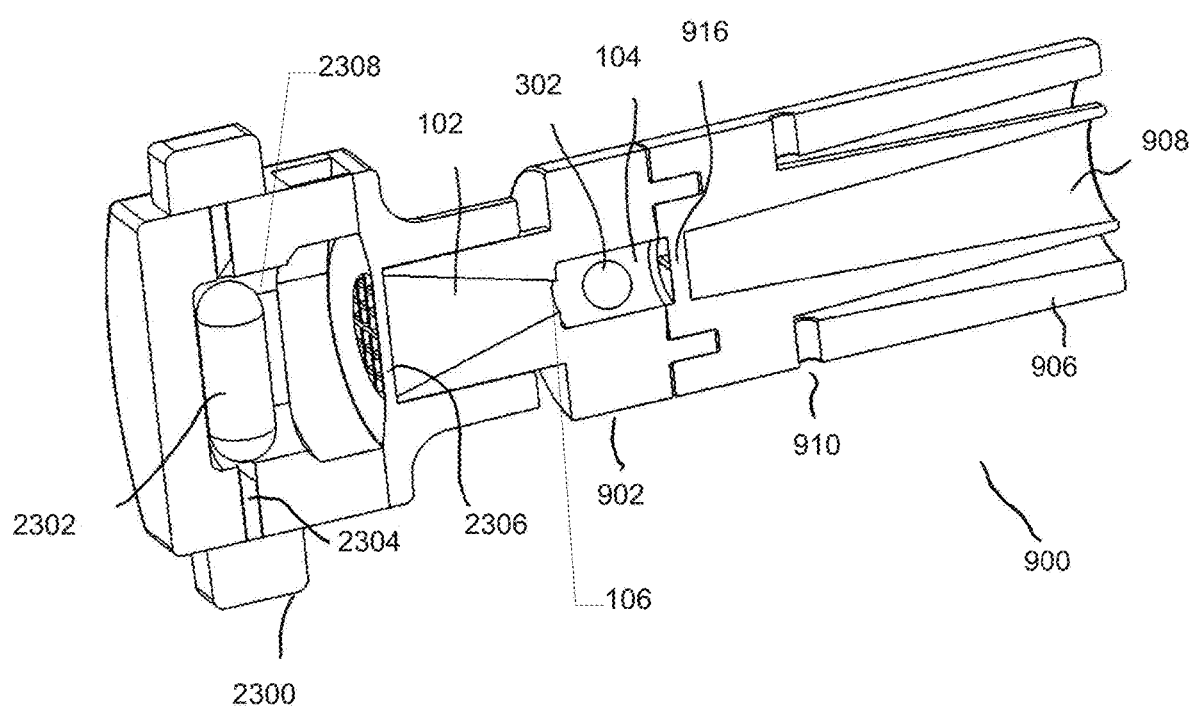
FIG. 24 shows a cross section of the DPI of FIG. 23.
Figure 25:
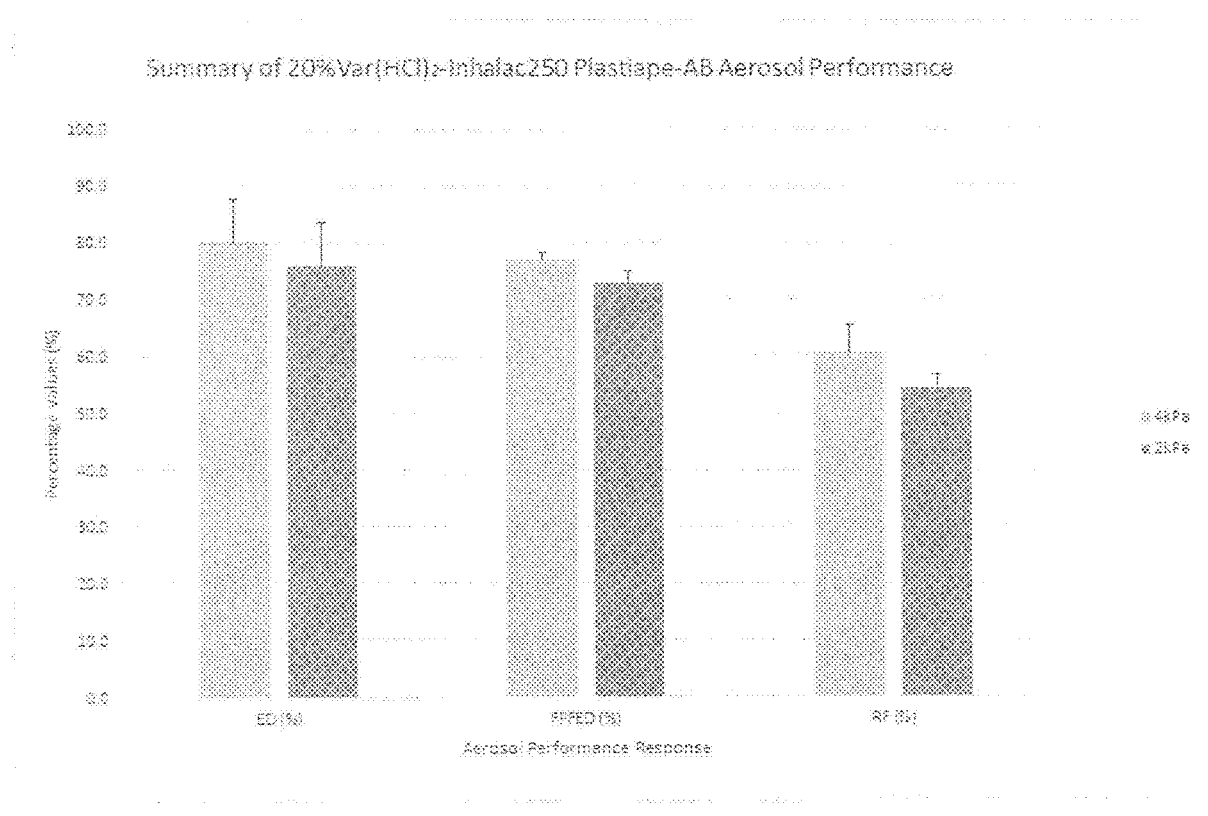

A specific embodiment of the inhaler 2300 has been created using the Plastiape RS01 dry powder inhaler (Plastiape S.p.a, Italy) as the dose containment and delivery system. This embodiment utilizes the capsule piercing and dose delivery system from a Plastiape RS01 to feed powder into the chamber with the oscillating actuator, a spherical bead as seen in FIGS. 23-24. After piercing a capsule 2302, air flows through inlet passages 2304 and the pierced capsule 2302 is lifted from the piercing chamber 2308 and rotates about its axis to efficiently empty the capsule 2302. The aerosolized powder exiting the rotating capsule 2302 flows through a grid that serves as a flow straightening element 2306 and is fed into the chamber with the oscillating spherical bead. The design utilizes a conical inlet from the Plastiape RS01 inhaler to the inlet diameter 106. Experiments using a Next Generation Impactor (NGI) with this design have shown an emitted fine particle fraction (% FPF, with a fine particle cutoff <5.3 µm) greater than 70% with several different active pharmaceutical ingredients (API). Emitted fine particle fraction (% FPF) is defined as the fraction of emitted mass below a cutoff diameter divided by the emitted mass from the inhaler. An experiment was performed testing this embodiment at 2 and 4 kPa with 20 mg 20% Vardenafil (HCl)$_2$ in a lactose blend. This inhaler 2300 used $d_{bead}$=4.00 mm, $d_{inlet}$=2.72 mm, $d_{chamber}$=5.89 mm, $l_{chamber}$=10 mm, with 2 bypass channels open which resulted in a resistance=0.104 (cm $H_2O^{0.5}$/LPM). Results show that this embodiment achieved similar aerosol performance at 2 and 4 kPa as shown in FIG. 25.

Figure 26:
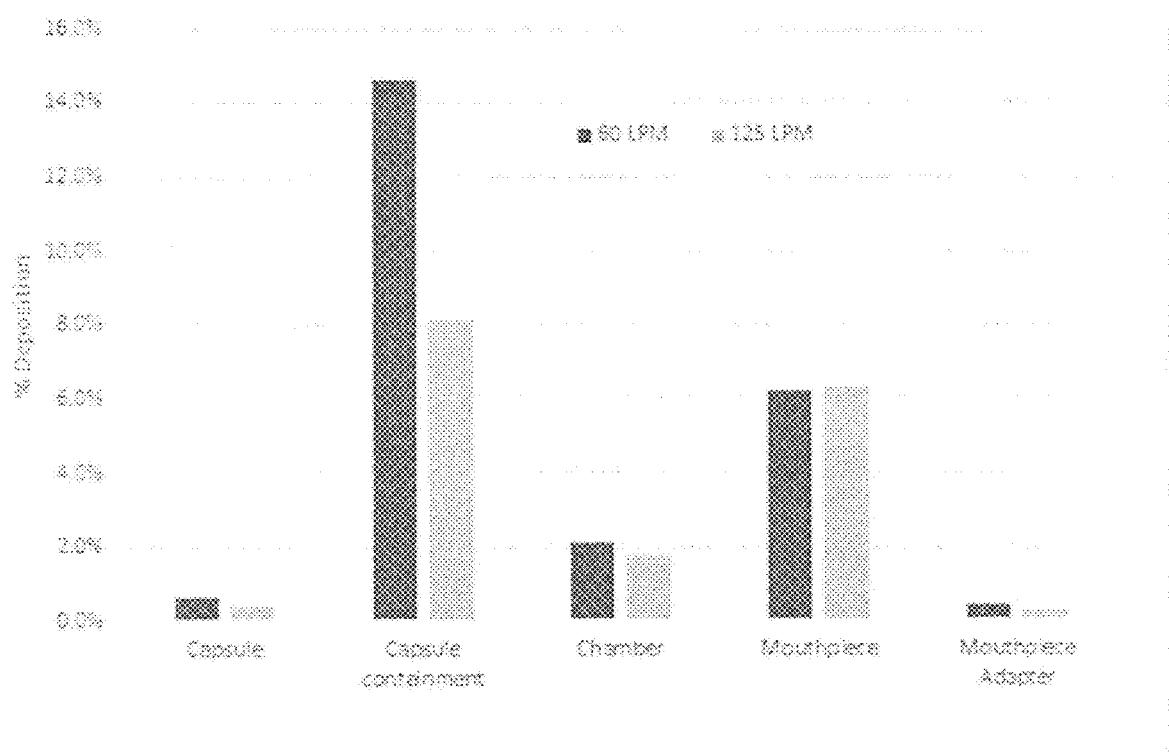
FIG. 26 shows drug deposition within the DPI of FIG. 23 at different flow rates.

Typically drug powder deposition on the inhaler device components in dry powder inhalers changes with air flow rate. An experiment was conducted using the embodiment exhibited in FIG. 23 and FIG. 24. This inhaler used $d_{bead}$=4.00 mm, $d_{inlet}$=2.72 mm, $d_{chamber}$=5.89 mm, $l_{chamber}$=10 mm, with 2 bypass channels which resulted in a resistance=0.104 (cm $H_2O^{0.5}$/LPM). The inhaler was loaded with 20 mg of 20% Vardenafil (HCl)$_2$ and the amount of drug deposited in the capsule containment 2300, dispersion chamber 104 and bead 302, and mouthpiece 406 components as shown in FIG. 26. The inhaler was tested at 60 and 150 LPM (4 and 24 kPa respectively). Surprisingly the drug deposition by % mass was largely unchanged in the dispersion chamber 104, bead 302, and mouthpiece 408 sections despite a 250% increase in inhaler flow as shown in TABLE 4.

TABLE 4

| Inhaler portion | 60 LPM | 150 LPM |
|---|---|---|
| Capsule containment | 14.6% | 8.1% |
| Chamber and bead | 2.1% | 1.7% |
| Mouthpiece | 6.2% | 6.3% |

Figure 27A:
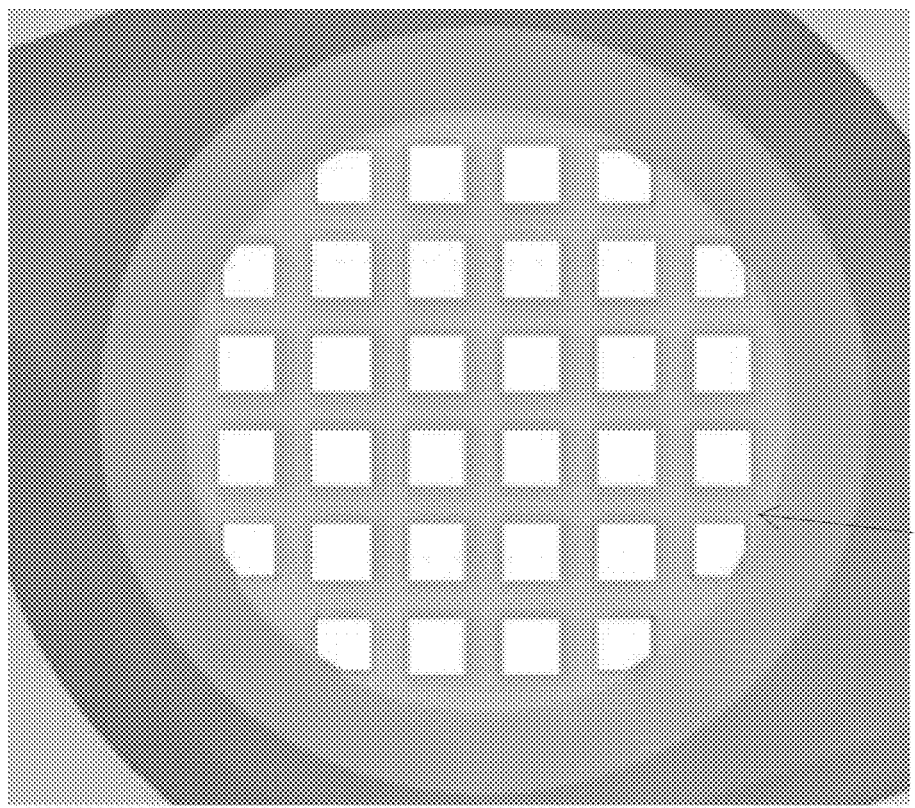
FIG. 27A shows a tightly-spaced grid structure used in experiment testing swirling flow according to embodiments.
Figure 27B:
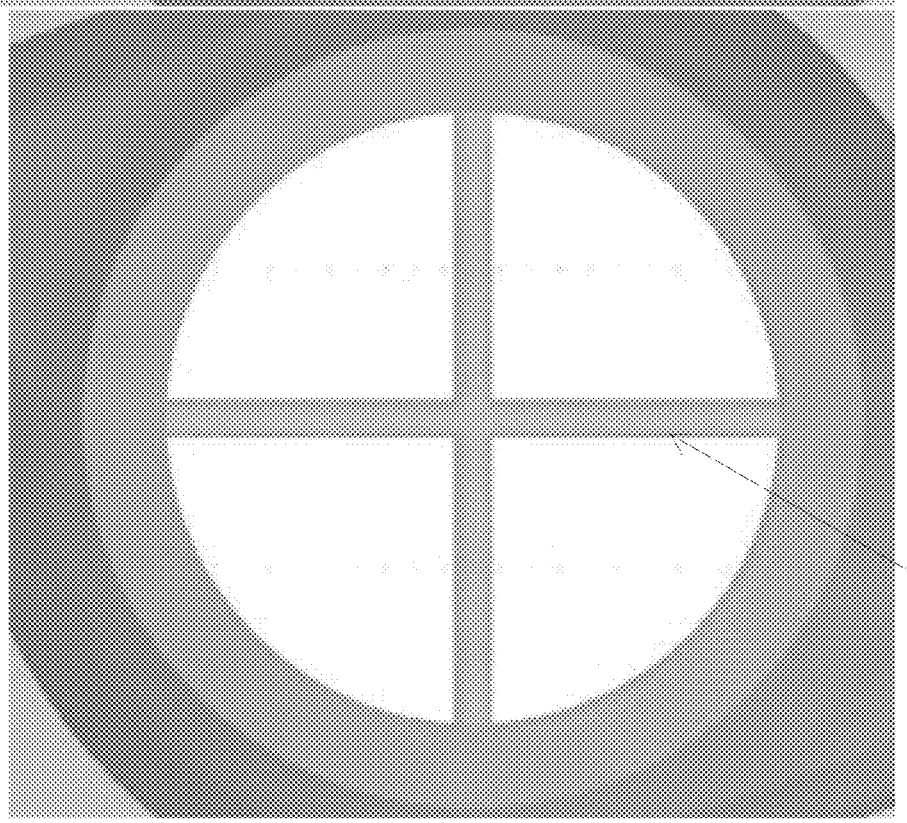
FIG. 27B shows a 2-piece grid structure used in experiment testing swirling flow according to embodiments.

An experiment was performed using an embodiment as illustrated in FIG. 24. This embodiment has air inlets that are tangential to flow through the chamber 104 and they are shaped to induce a swirling or tangential flow which promotes capsule emptying. A grid is in place 2306 and it acts as a flow straightener similar to a honeycomb flow straightener. Two different grids were tested (1) a tightly-spaced grid 2700 of FIG. 27A and (2) simple 2-piece grid structure 2702 as shown in FIG. 27B. The tightly-spaced grid 2700 straightens and aligns the flow in axial direction similar to a honeycomb flow straightener used in wind tunnels. The tightly-spaced grid 2700 aligns the flow along the axis L4 shown in FIG. 2B. The simple 2-piece grid 2702 provides little to no straightening of the flow. It was found that using the simple 2-piece grid 2702 prevented a spherical bead from oscillating under any flow conditions. The bead remained hovering near the inlet and did not oscillate.

What is claimed is:

1. A dry powder inhaler, comprising:
    a powder storage element configured to hold a powdered medicament, wherein the powdered medicament is packaged in one or more blisters or one or more capsules;
    a piercing member configured to puncture the one or more blisters or the one or more capsules;
    an inlet channel configured to receive powdered medicament from the powder storage element that is entrained in an airflow, the inlet channel having a portion with a first diameter and defining an opening, wherein the inlet channel comprises a proximal end and a distal end, wherein the proximal end is positioned nearer to the powder storage element;
    a grid coupled with the proximal end of the inlet channel;
    a dispersion chamber that is adapted to receive the airflow and the powdered medicament from the distal end of the inlet channel, the dispersion chamber having a second diameter, wherein:
        the inlet channel extends an entire distance between the powder storage element and the dispersion chamber; and
        the inlet channel comprises continuous interior walls that extend from the grid to the dispersion chamber such that air is prevented from entering the inlet channel except through the proximal end of the inlet channel;
    an actuator housed within the dispersion chamber, the actuator being configured to oscillate within the dispersion chamber when exposed to the airflow to deaggregate the powdered medicament entrained in the airflow passing through the dispersion chamber, wherein a ratio between the first diameter and the second diameter is between about 0.40 and 0.60 such that an audible sound is produced as the actuator oscillates; and
    an outlet channel through which the airflow and powdered medicament exit the inhaler for delivery to a patient.

2. The dry powder inhaler according to claim 1, wherein:
    the dispersion chamber has a length; and
    the actuator has a diameter, and the length of the dispersion chamber is between about 2 and 3.5 times larger than the diameter of the actuator such that an audible sound is produced as the actuator oscillates.

3. The dry powder inhaler according to claim 1, wherein the dispersion chamber defines at least one aperture configured to receive chase air separate from the airflow entering in through the inlet channel.

4. A dry powder inhaler, comprising:
    a powder storage element configured to hold a powdered medicament;
    an inlet channel configured to receive powdered medicament from the powder storage element that is entrained in an airflow, the inlet channel having a portion with a first diameter and defining an opening, wherein the inlet channel comprises a proximal end and a distal end, wherein the proximal end is positioned nearer to the powder storage element;
    a grid coupled with the proximal end of the inlet channel;

a dispersion chamber defining an uninterrupted surface of cylindrical cross-section that is adapted to receive the airflow and the powdered medicament from the distal end of the inlet channel, the dispersion chamber having a second diameter;

an actuator housed within the dispersion chamber, the actuator being configured to oscillate within the dispersion chamber when exposed to the airflow to deaggregate the powdered medicament entrained in the airflow passing through the dispersion chamber, wherein a ratio between the first diameter and the second diameter is between about 0.40 and 0.60 such that an audible sound is produced as the actuator oscillates; and an outlet channel through which the airflow and powdered medicament exit the inhaler for delivery to a patient;

wherein:

the inlet channel extends an entire distance between the powder storage element and the dispersion chamber; and the inhaler comprises continuous interior walls that extend from the grid to an end of the dispersion chamber nearest the outlet channel such that air is prevented from entering the inlet channel except through the proximal end of the inlet channel.

* * * * *